United States Patent [19]
Keogh et al.

[11] Patent Number: 5,545,213
[45] Date of Patent: Aug. 13, 1996

[54] METHOD FOR ADMINISTERING A BIOACTIVE AGENT

[75] Inventors: James R. Keogh, Maplewood; Christopher M. Hobot, Tonka Bay, both of Minn.; John W. Eaton, Troy, N.Y.; Allan H. Jevne, Anoka; Matthew A. Bergan, Brooklyn Park, both of Minn.

[73] Assignee: Medtronic, Inc., Minneapolis, Minn.

[21] Appl. No.: 430,063

[22] Filed: Apr. 27, 1995

Related U.S. Application Data

[62] Division of Ser. No. 255,632, Jun. 9, 1994, Pat. No. 5,476,509, which is a division of Ser. No. 969,692, Oct. 30, 1992, Pat. No. 5,344,455.

[51] Int. Cl.$^6$ ........................................... A61F 2/06
[52] U.S. Cl. ........................ 623/1; 623/11; 623/901; 604/266
[58] Field of Search ........................ 623/1, 11, 12, 623/901; 604/266; 606/76

[56] References Cited

U.S. PATENT DOCUMENTS

| | | |
|---|---|---|
| 3,826,678 | 7/1974 | Hoffman . |
| 4,442,133 | 4/1984 | Greco . |
| 4,459,318 | 7/1984 | Hyans . |
| 4,612,337 | 9/1986 | Fox, Jr. . |
| 4,743,258 | 5/1988 | Ikada et al. ........................ 623/1 |
| 4,829,098 | 5/1989 | Hoffman . |
| 4,879,135 | 11/1989 | Greco et al. ........................ 623/1 |
| 4,895,566 | 1/1990 | Lee . |
| 5,004,461 | 4/1991 | Wilson . |
| 5,080,924 | 1/1992 | Kamel . |
| 5,229,172 | 7/1993 | Cahalan . |
| 5,263,992 | 11/1993 | Guire ........................ 604/266 |
| 5,344,455 | 9/1994 | Keogh et al. ........................ 623/1 |
| 5,476,509 | 12/1995 | Keogh et al. ........................ 623/1 |

FOREIGN PATENT DOCUMENTS

| | | |
|---|---|---|
| 0184465 | 6/1986 | European Pat. Off. . |
| 0294905 | 12/1988 | European Pat. Off. . |
| 0470443 | 2/1992 | European Pat. Off. . |
| 0519087 | 12/1992 | European Pat. Off. . |
| 8700060 | 1/1987 | WIPO . |
| 9116932 | 11/1991 | WIPO . |
| 9211877 | 7/1992 | WIPO . |

OTHER PUBLICATIONS

*Cell Behavior on Polymer Surfaces Grafted with Non–Ionic Monomers*, by Akio Kishida et al., Biomaterials, 1991, vol. 12, Oct.

*Photoinitiated Graft Copolymerization of Hydroxyethyl Methacryla (HEMA) onto Cotton Cellulose*, S. R. Shukla et al., Journal of Applied Polymer Schience, vol. 42, 2163–2168 (1991).

*Surface Modification of Polymers V. Biomaterial Applications*, by Klas Allmer et al., Journal of Polymer Science: Part A: Polymer Chemistry, vol. 28, 173–183 (1990).

*Anticoagulation Activity of the Modified Polyvinyl Alcohol*, by Heung–Jae Chun et al., Polymer Journal, vol. 22, No. 4, pp. 347–354 (1990).

*Surface Modification of Polymers. II. Grafting with Glycidyl Acrylates and the Reactions of the Grafted Surfaces with Amines*, by Klas Allmer et al., Journal of Polymer Science: Part A: Polymer Chemistry, vol. 27, 1641–162 (1989).

*Reactive Site and Mechanism of Graft Copolymerization onto Poly(ether urethane) with Ceric Ion as Initiator*, by X. D. Feng et al., Macromolecules, vol. 18, No. 11 (1985).

(List continued on next page.)

Primary Examiner—Paul B. Prebilic
Attorney, Agent, or Firm—Daniel W. Latham; Harold R. Patton

[57] ABSTRACT

Articles having a graft polymer with a net ionic charge bonded to a polymeric substrate surface provide an improved method for administering a bioactive agent having a net ionic charge. The [articles are] method is especially useful [as] for thromboresistant and/or antimicrobial medical devices.

8 Claims, 15 Drawing Sheets

OTHER PUBLICATIONS

*Surface Modification of Polymers. I. Vapour Phase Photografting with Acrylic Acid,* by K. Allmer et al., Journal of Polymer Science: Part A: Polymer Chemistry, vol. 26, 2099–2111 (1988).

*Surface Modification of Silicone for Tissue Adhesion,* by T. Okada et al., Biomaterials and Clinical Applications, Amsterdam, 1987, p. 465.

*Modification of Polymer Surfaces by Photoinduced Graft Copolymerization,* by B. Ranby et al., ASC Symposium Series 364, 1988, pp. 168–186.

*Synthetic Hydrogels for Biomedical Applications,* by Buddy D. Ratner and Allan S. Hoffman, Publication entitled Hydrogels For Medical and Related Applications, in American Chemical Society (1975).

- WHERE R IS EITHER H OR CH$_3$
- WHERE R' IS EITHER H OR CH$_3$
- WHERE X IS THE HYDROPHILIC SUBSTITUENT
- WHERE Y IS THE BIOAGENT COUPLING SUBSTITUENT
- WHERE M IS THE NUMBER OF BIOCOMPATIBLE HYDROPHILIC SPACER UNITS
- WHERE N IS THE NUMBER OF BIOCOMPATIBLE/BIOACTIVE UNITS

METHOD FOR ADMINISTERING A BIOACTIVE AGENT

This is a divisional of Ser. No. 08/255,632 filed Jun. 9, 1994, now U.S. Pat. No. 5,476,509 which is a division of Ser. No. 07/969,692 filed Oct. 30, 1992, now U.S. Pat. No. 5,344,455.

BACKGROUND OF THE INVENTION

For over forty years a number of medical devices which contact the blood or blood products of living persons or animals have been developed, manufactured and used clinically. A partial list of such articles would include pacemakers, arterial grafts, heart valves, artificial hearts, heart pumps, hip protheses, heart lung machines, catheters and kidney dialysis equipment.

A major problem with such articles is that their working surfaces, (i.e., surfaces which contact blood or blood products, including, serum, plasma and other fluids and solids derived from blood), are foreign to blood and blood products and tend to initiate, among other things, red cell destruction and coagulation of blood to form clots (thrombogenesis).

Normal intact endothelium is nonthrombogenic due partly to the synthesis of heparan sulfate. Heparan sulfate tends to remain bound to the surface of endothelial cells accelerating the inactivation of thrombin, the enzyme responsible for the polymerization of fibrinogen to fibrin in clot formation, by antithrombin III (ATIII). Heparan sulfate is a very powerful anticoagulant in the natural vasculature. Consequently, it has been of great interest to physicians and the medical industry to devise blood-contacting polymeric surfaces that possess characteristics of heparan sulfate, specifically by coating surfaces with heparin. For example, in U.S. Pat. No. 3,826,678 to Hoffman et al., biologically active molecules are chemically bonded to polymers and copolymers which previously have been radiation-grafted to inert polymeric substrates such as a polyurethane and polyethylene. The grafted polymer is preferably a hydrophilic hydrogel (e.g. HEMA) and may include heparin bonded to the hydrogel.

Another major problem with such articles is their susceptibility to post-implant infection. *Staph. epidermidis*, which exists on human skin and *Staph. aureus*, sometimes found in hospital environments, are the two most frequent pathogens encountered in implant and similar situations. They both have the ability to enter the body through the surgical opening and attack the implant site. This problem has been addressed, for example, in U.S. Pat. No. 4,442,133 to Greco et al. in which a PTFE or Dacron graft is soaked in TDMAC (tridodecyl methyl ammonium chloride) dissolved in ethanol. The TDMAC is absorbed to form a coating and then incubated in a solution of antibiotic e.g. penicillin or cefoxitin. Also, for example, in U.S. Pat. No. 4,612,337 to Fox, Jr., et al., a polymeric material such as (PTFE) is soaked in antibiotic solutions with an organic solvent, then soaked in an organic solvent with a metal salt followed by a resoak in the antibiotic/organic solvent solution.

There is therefore a clear need for new and improved thromboresistant and infection resistant articles. This need can be met by providing such articles with antimicrobial agents which can result in bactericidal activity of that polymer or with anticoagulant agents to impart thromboresistance. It is also sometimes desirable to include bioactive agents other than antimicrobials and anticoagulants in such articles. This invention is directed to those ends.

SUMMARY OF THE INVENTION

We have discovered that an article can be made for use in contact with blood or blood products, the blood-contacting polymeric surface of the article having grafted thereto a graft polymer selected from acrylic acid (AA), acrylamide (AAm), N-(3-aminopropyl) methacrylamide hydrochloride (APMA) or 2-acrylamido-2-methylpropane sulfonic acid (AMPS) and copolymers thereof, and a bioactive agent coupled to the graft polymer. The bioactive agent can be ionically or covalently coupled to the graft polymer and can be an antibiotic or antimicrobial such as silver or gentamycin. The polymeric surface of the article can be a polyurethane such as a polyetherurethane. The advantages provided by such an article involve features of both hydrophilic coatings and bioactive agents. For example, antimicrobials are able to fight post-implant infections while hydrophilic coatings such as an AMPS-containing coatings are able to reduce thrombosis and provide slippery surfaces.

In one aspect of the invention, the graft polymer includes pendant groups having an ionic charge and the bioactive agent has an ionically opposite charge to the graft polymer pendant groups. For example, the graft polymer could be AMPS or APMA and the bioactive agent could be gentamycin or basic fibroblast growth factor (bFGF). The bioactive agent is thereby maintained on the article by ionic attraction. In another aspect of the invention, the bioactive agent has the same charge as the pendant groups of the graft polymer. The bioactive agent is therefore repelled and released from the surface of the article into the blood. Thus, according to the present invention, a charged surface can be used for administering a bioactive agent having a net ionic charge to a patient by preparing an aqueous solution of monomers which include pendant amine or acid groups capable of imparting a net (+) or (−) ionic charge in a graft polymer and a neutral, hydrophilic monomer to produce a copolymer on a polymeric surface and then placing the charged bioactive agent onto the grafted surface and implanting the polymeric surface and bioactive agent into the patient's body.

In yet another aspect of the invention, the interaction between the article exposed to the body and a bioactive agent administered to the body can be controlled by controlling the relative charges of the article and the bioactive agent. Where the agent has a (+) or (−) net ionic charge, a graft polymer can be provided on the exposed parts of the article which has a net ionic charge the same as that of the agent thereby preventing ionic attraction between the article and the administered agent. Thus, according to the present invention, a charged surface can be used to prevent interactions with a bioactive agent having a net ionic charge which is administered to a patient by using an aqueous solution of monomers which include pendant amine or acid groups capable of imparting a net (+) or (−) ionic charge in a graft polymer and a neutral, hydrophilic monomer to produce a copolymer on a polymeric surface and then implanting the grafted polymeric surface into the patient's body and administering the bioactive agent of the same charge to the patient.

In yet another apect of the invention, an albumin-binding dye such as blue dextran is the bioactive agent and can be ionically or covalently attached to a graft polymer such as an APMA/AAm copolymer. The surface then attracts albumin from the blood contacting the surface of the article.

In yet another aspect of the invention, the graft polymer provides control of hydrophilicity and coupling of the bioactive agent by selecting monomers for the graft polymer from AAm, AA, AMPS, HEMA and APMA in predetermined relative amounts. For example, a copolymer of APMA and AAm can be grafted onto a polyurethane surface and heparin can be coupled to the grafted copolymer.

DETAILED DESCRIPTION OF THE INVENTION

Figure 1:
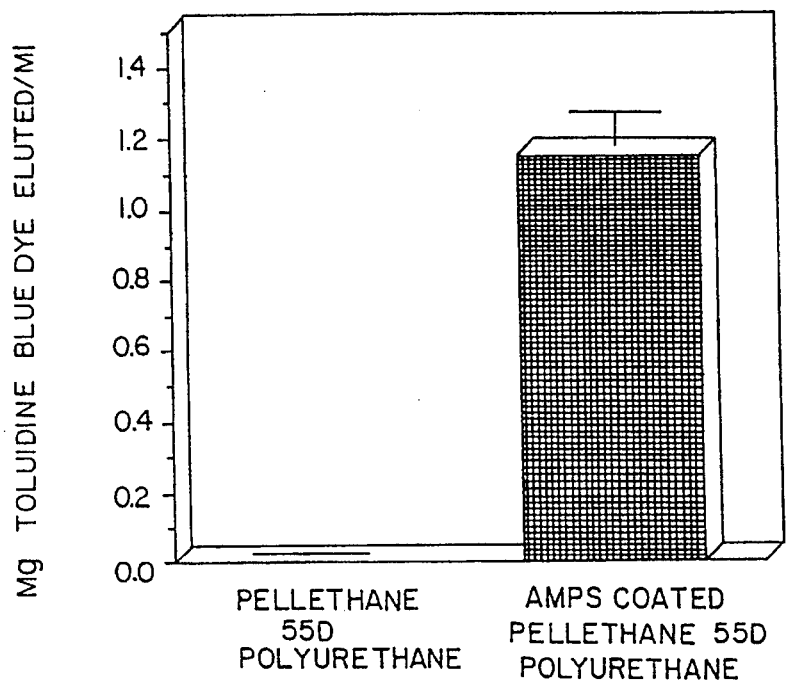
FIG. 1 is a graph showing the amount of toluidine blue dye released from the surfaces of Pellethane 55D polyurethane and Pellethane 55D polyurethane grafted with AMPS.

The invention is aimed at simultaneously solving a number of problems with implantable articles. The invention involves features of hydrophilic coatings and bioactive agents, such as antimicrobials, which are able to fight post-implant infections as well as thrombosis while providing slippery surfaces. Other bioactive agents are contemplated as well.

The substrate of a working surface of an article intended for contact with blood or blood product will be comprised of a biologically inert polymeric material. According to the invention a hydrophilic graft polymer having a net charge due to pendant anionic or cationic groups thereon will be permanently covalently bonded by graft polymerization to the substrate. Such graft polymers can be selected to provide thromboresistant slip coatings which lend themselves to ionic coupling, (when selected to provide an appropriate charge dissimilar to that of the bioactive agent) with various bioactive agents, which are selected due to their ionic nature. Ionic coupling of the bioactive agent to the graft polymer may be achieved by simply immersing the surface-grafted polymer in a solution of the desired bioactive agent. Another aspect of the invention allows one to select graft polymers having a charge similar to the bioactive agent to assure non-attachment therebetween. Other graft polymers can be selected to provide hydrophilic slip coatings which lend themselves to covalent coupling (when selected to provide a functional chemical group appropriate for the covalent attachment of the bioactive agent) with bioactive agents.

The various articles contemplated by this invention may be provided by solid-phase polymeric substrates selected from the group of materials shown in Table 1 below.

TABLE 1

Polyamides
Polycarbonates
Polyethers
Polyesters
Polyolefins
Polystyrene
Polyurethane
Polyvinyl chlorides
Silicones
Polyethylenes
Polypropylenes
Polyisoprenes
Polytetrafluoroethylenes At the present time it is believed that polyurethane provides the preferred polymeric substrate in the context of this invention.

The graft polymer to be used originates with a grafting monomer which is hydrophilic. Such monomers create a hydrophilic polymer coating on the substrate surface. A hydrophilic coating minimizes protein interactions and also provides slip properties to the surface. The monomer must contain at least one vinyl group. The vinyl group is necessary for free radical polymerization to occur. The monomer may be neutral, anionic or cationic. After grafting (and if necessary following chemical modification) the resultant grafted polymer should have a net positive or net negative charge. The charge allows the ionic attachment of oppositely charged bioactive molecules. Neutral monomers may be chemically modified after grafting to yield anionic or cationic surfaces. For example, grafted acrylamide may be hydrolyzed to acrylic acid thus forming an anionic surface.

Specifically, a number of graft slip coatings have been used according to this invention. The most preferred are comprised of monomers grafted onto the substrate surface via ceric ion initiation. Monomers with cationic as well as anionic pendant groups have been grafted. An example of the former is N-(3-aminopropyl) methacrylate (APMA) and copolymers thereof while a prime example of the latter is 2-acrylamido- 2-methyl propane sulfonic acid (AMPS).

These charged surfaces lend themselves to the ionic coupling of charged bioactive agents. The ionic coupling of the bioactive agents has the advantage of slowly releasing these agents under appropriate conditions. Examples of antimicrobial bioactive agents are gentamycin sulfate and silver ion. Generally, bioactive agents selected from the types shown in Table 2 may be used according to this invention for ionic or covalent coupling.

TABLE 2

Antibacterial agents or antimicrobial agents
Anticoagulants
Enzymes
Catalysts
Hormones
Growth factors
Lectins Drugs
Vitamins
Antibodies
Antigens
Nucleic acids
Dyes—which act as biological ligands
DNA and RNA segments
Proteins
Peptides While ceric ion initiation (CeIV) is presently most preferred as the technique to be used to graft monomers to substrate surfaces, other grafting techniques are well known and may be used in appropriate situations. For example, corona discharge, UV irradiation and ionizing radiation ($^{60}$Co, X-rays, high energy electrons, plasma gas discharge) are known. These grafting techniques are examples of how to form free radicals on a polymer substrate working surface. The free radicals formed thereon initiate the grafting of vinyl ($CH_2=CH—R$) type monomers.

The ionic coupling of bioactive agents is achieved by simply immersing the surface-grafted polymer in a solution of the desired bioactive agent. For example, in the case of antimicrobials, bactericidal (ring of inhibition) testing was performed on AMPS/$AgNO_3$ and AMPS/gentamycin sulfate surfaces. Significant antibacterial activity was achieved. In the case of the AMPS/gentamycin sulfate surface, full activity was retained even after a 24 hour DI water rinse.

Although the detailed discussion below mentions Examples in which treatment is on films as the polymeric substrate surface, it is not intended that this invention be so limited. Grafted hydrophilic surfaces ionically coupled with bioactive agents may be similarly bound to other substrate surfaces, i.e., surfaces of articles intended to contact blood or blood products, of articles of any shape or form including tubular, sheet, rod and articles of proper shape for use in artificial organs, blood handling equipment or bodily implants of any kind and to any encapsulant means therefor.

AMPS THROMBORESISTANT COATING

As already indicated, normal intact endothelium is non-thrombogenic due partly to the synthesis of heparan sulfate. This heparan sulfate tends to remain bound to the surface of endothelial cells, accelerating the inactivation of thrombin, the enzyme responsible for the polymerization of fibrinogen to fibrin in clot formation, by ATIII. Heparan sulfate is a very powerful anticoagulant in the natural vasculature.

Heparin is a strongly acidic glycosaminoglycan. It has a high content of N— and O— sulfate groups. Heparin is structurally similar to heparan sulfate although it is more sulfated. The anticoagulant activity of heparin is directly dependent on its molecular size and electric charge, thus increasing the molecular weight and/or the amount of sulfonation will increase the anticoagulant activity. Therefore, it is felt a highly sulfonated polymer surface may stimulate the inactivation of thrombin by ATIII, similar to heparin.

The 2-acrylamido-2-methylpropane sulfonic acid (AMPS) coating is aimed at producing a surface that will decrease the nonspecific adsorption of various proteins due to its hydrophilicity and provide a highly sulfonated surface that will preferentially adsorb ATIII.

Much of the AMPS work effort relative to this invention went into developing a general AMPS surface modification technique for polyurethanes, however, the technique may be used for other material surfaces with a few modifications. The technique developed is based on the generation of free radicals on a polyurethane surface with CeIV ion and the graft copolymerization of AMPS monomers directly to that surface.

EXAMPLE I

Extruded Pellethane 55D polyurethane was used as a polyurethane material. It is available from the Dow Chemical Company of Midland, Mich. 48640. Films of the 55D polyurethane were extracted in acetone for 72 hours and ethanol for another 72 hours prior to CeIV ion grafting. The solvent extraction process removes any processing aids that might interfere with the grafting process. A 50% AMPS monomer solution in DI water was prepared and 20 ml of CeIV ion solution per 100 ml of monomer solution was added. The CeIV ion solution consisted of 2.74 g ceric ammonium nitrate and 3.15 g nitric acid in 50 ml DI water. The CeIV-monomer solution was then degassed and released to nitrogen prior to grafting. Pallethane 55D polyurethane samples were placed into the degassed monomer solutions and stirred. Grafting was allowed to proceed for 2 hours. Grafted samples were then removed and thoroughly washed in DI water.

The presence of sulfonic acid groups on AMPS grafted material was measured using toluidine blue dye. Being positively charged, toluidine blue dye will ionically associate with negatively charged surfaces. Therefore, the binding of toluidine blue dye to the AMPS surface indicates the presence of negative charges due to the sulfonic acid groups in AMPS. PS grafted samples were therefore placed into a 1% toluidine blue dye/DI water solution for 1 minute and then rinsed in DI water. The bound dye was then released from the surface using a 1% sodium dodecylsulfate (SDS) in DI water solution. The amount of dye eluted was determined spectrophotometrically at 640 nm. The amount of dye released from Pellethane 55D samples and Pelletbane 55D samples grafted with AMPS is shown in FIG. 1.

As the results indicate Pallethane 55D containing no AMPS adsorbed no toluidine blue dye. This is due to the fact that Pellethane 55D contains no negatively charged groups. However, the AMPS coating adsorbed a large amount of toluidine blue dye indicating the presence of sulfonic acid groups on the surface. Because the AMPS surface contained a large amount of sulfonation, its ability to bind ATIII was investigated next.

EXAMPLE 2

Since clotting may be retarded on AMPS surface coated materials by the activation of ATIII by the sulfonic acid groups present on the modified polymer substrate surface, the surface-mediated activation of ATIII by AMPS coated samples was assessed. Samples were first rinsed in phosphate-buffered saline solution (PBS) for 15 minutes prior to ATIII exposure. Following rinsing, the samples were exposed for 15 minutes to an excess of purified ATIII (50 IU/ml). Non-adsorbed ATIII was removed by rapid rinsing in tris-buffered saline, pH 7.4 at 25° C. (100 mM NaCl and 50 mM tris). The amount of surface bound and activated ATIII was then estimated by incubating the samples with an excess of thrombin. After a 10 minute incubation with constant mixing at 25° C., the residual thrombin was measured by reaction with a chromogenic substrate (H-D-phenylalanyl-L-pipecolyl-L-arginine-p-nitroanilide dichloride) in a spectrophotometer. The change in absorbance at 405 nm was then measured.

Figure 2:
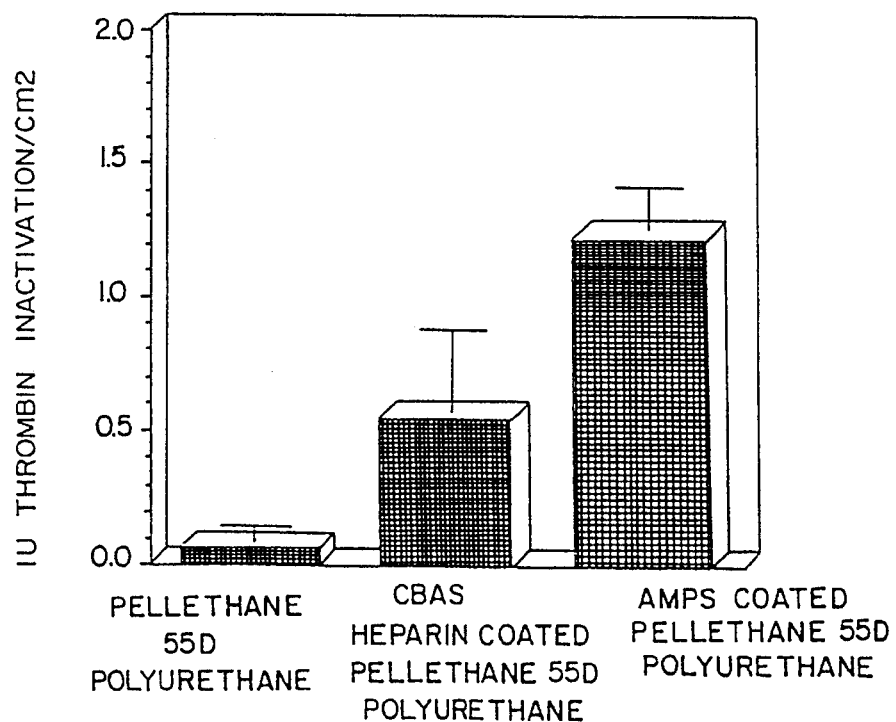
FIG. 2 is a graph showing a comparison of ATIII activity of uncoated Pollethane 55D polyurethane, heparin-coated Pellethane 55D polyurethane and AMPS coated Pellethane 55D polyurethane samples. The results are expressed as the amount of thrombin inactivated by the sample surfaces/cm$^2$.

The results are given in FIG. 2. As the results demonstrate, the AMPS surface derivatization appears to have some heparin-like activity. In fact, the AMPS coated samples appear to have more ATIII activity then CBAS® coated (Carmeda® Bioactive Surface) polyurethane samples. CBAS® is a heparin coating available from Carmeda AB, a Swedish company. This heparin-like effect is due to the sulfonic acid groups present in the AMPS coating.

It is therefore expected that the PS coating will possess nonthrombogenic properties usually associated with heparin coated materials.

AMPS/GENTAMYCIN INFECTION-RESISTANT COATING

One major problem with implantable polymeric devices is their susceptibility to post-implant infection. *Staph. epidermidis,* which exists on human skin, and *Staph. aureus,* sometimes found in hospital environments, are the two most frequent pathogens. They both have the ability to enter the body through the surgical opening and attack an implant site. Though the chance of this happening can be minimized through good surgical techniques and clean operating room environment, it cannot be totally eliminated. Furthermore, the consequences of post-implant infection are almost always severe. Up to 5% of implants (depending on the device implanted) become infected; morbidity/mortality is most often the result.

Most prototype work to date on antimicrobial additions to AMPS surfaces has been done with gentamycin. It has been determined that it has the ability to ionically bond to the AMPS coating. Commercially, gentamycin is most frequently available as a sulfated salt. Since AMPS contains a sulfonic acid functionality, it was found that immersion of AMPS-coated polymer into a gentamycin sulfate solution resulted in the adsorption of gentamycin to the surface. Furthermore, in vitro, the adsorbed gentamycin eluted from the surface, thus giving the AMPS surface a bactericidal activity. As a result, the proper addition of antimicrobials to the AMPS coatings resulted in an infection-resistant as well as nonthrombogenic coating.

EXAMPLE 3

The procedure for loading the AMPS surfaces with gentamycin was as follows. An AMPS surface was created on a polymer substrate as described above. The AMPS-coated polymers were then immersed in an aqueous (normally 5% w/w) solution of gentamycin sulfate; this immersion may be for as little as 3 minutes. Upon completion of the immersion, the samples were removed, rinsed for 10–15 seconds in DI water, allowed to air dry, and stored.

Samples were analyzed for antibacterial activity using the "ring of inhibition" test. The ring of inhibition test is well known in the literature as an in vitro test of the antibacterial efficacy of a drug or drug-loaded system. It is set up and run as follows. A blood agar plate is cultured with the test bacterial organism and incubated overnight. One or two colonies from this plate are then swabbed and stirred into TSB solution to a standard turbidity ($1.5 \times 10^9$/ml using Macfarland standards). This bacterial solution is then streaked on a Mueller-Hinton agar plate. The samples to be tested are then pressed onto or imbedded into the agar, along with one positive and one negative control. The positive control should be a drug-loaded sample with well-defined antibacterial properties; the negative control should be a sample containing no drug. One or two samples (depending on their size) can then be tested on the same plate. Once the agar is loaded with samples, it is turned upside down and incubated at 37° C. overnight. The following day the plate may be removed from incubation and the ring of bacterial inhibition around each sample measured. The regions of bacterial growth and inhibition are obvious visually. The normal cloudy appearance of bacteria on agar is totally absent in the areas of inhibited growth. The ring of inhibition is simply measured with a ruler (if the "ring" is oblong, an approximate average radius of inhibition is taken). The ring of inhibition analysis is a good measure of the relative efficacy of various drug-loaded materials.

*S. epidermidis* was the test organism of all ring of inhibition testing done in connection with AMPS-coated polymers as described herein.

Figure 3:
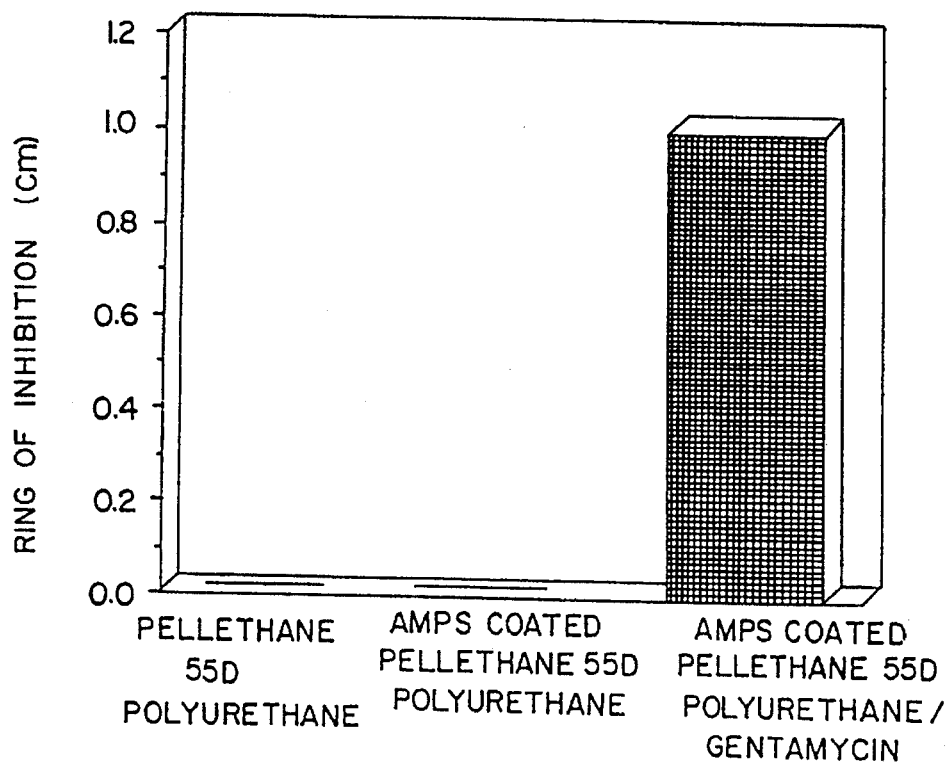
FIG. 3 is a graph showing ring of inhibition of Pellethane 55D polyurethane, AMPS coated Pellethane 55D polyurethane and AMPS coated Pellethane 55D polyurethanes containing adsorbed gentamycin. Bacteria used were *S. epidermidis*.

The graph of FIG. 3 demonstrates the bactericidal properties of AMPS coatings containing adsorbed gentamycin. FIG. 3 shows the comparative efficacy vs. *S. epidermidis* of Pallethane 55D polyurethane, 55D polyurethane with AMPS grafted coating, and AMPS coated Pallethane 55D polyurethane with adsorbed gentamycin.

As the results indicate in FIG. 3, there were no bactericidal properties associated with the plain Pellethane 55D polyurethane or the AMPS grafted Pellethane 55D polyurethane, however, the AMPS grafted Pallethane 55D polyurethane containing adsorbed gentamycin demonstrated a significant bactericidal activity. The ability of the gentamycin to elute from the AMPS grafted surfaces under different ionic conditions was investigated next.

Figure 4:
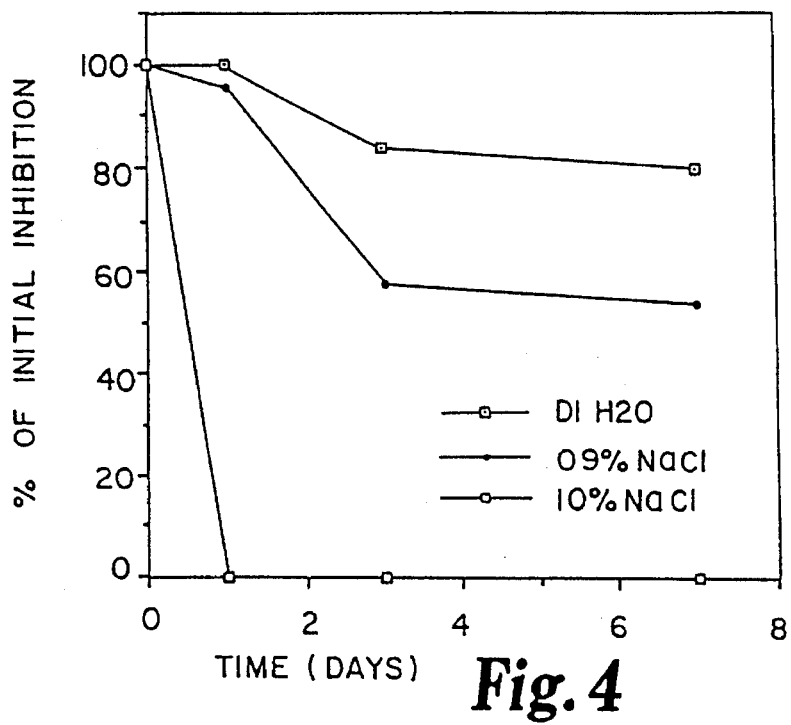
FIG. 4 is a graph showing elution rate of gentamycin from AMPS grafted Pellethane 55D polyurethane samples in deionized (DI) water, 0.9% NaCl solution and 10% NaCl solution as measured by ring of inhibition.

FIG. 4 shows the results of an elution test done to determine how ionic strength affects the rate of elution of gentamycin from the AMPS coating. Note that the greater the ionic strength of the storage solution, the faster the ring of inhibition decreases, and therefore, the faster the rate of gentamycin elution from the surface. This not only indicates that ionic bonding of drug to coating has occurred, but that at a physiological ionic strength (0.9% concentration), the rate of desorption is conducive to a long-term, slow release of drug. These kinetics are remarkably similar to those of diffusion of drug from a bulk-loaded matrix, indicating that therapeutic amounts of drug will release over a relatively long period of time.

EXAMPLE 4

The following Example was prepared to determine if the adsorption of gentamycin would decrease the ATIII activity of an AMPS coated surface. It consists of loading AMPS grafted surfaces with gentamycin via immersion in an aqueous (normally 5% w/w) solution of gentamycin sulfate for 5 minutes. Upon completion of the immersion in gentamycin, the samples were removed, rinsed for 10–15 seconds in DI water and either dried or placed into a 10% NaCl solution for 24 hours. Samples were than analyzed for ATIII activity.

Figure 5:
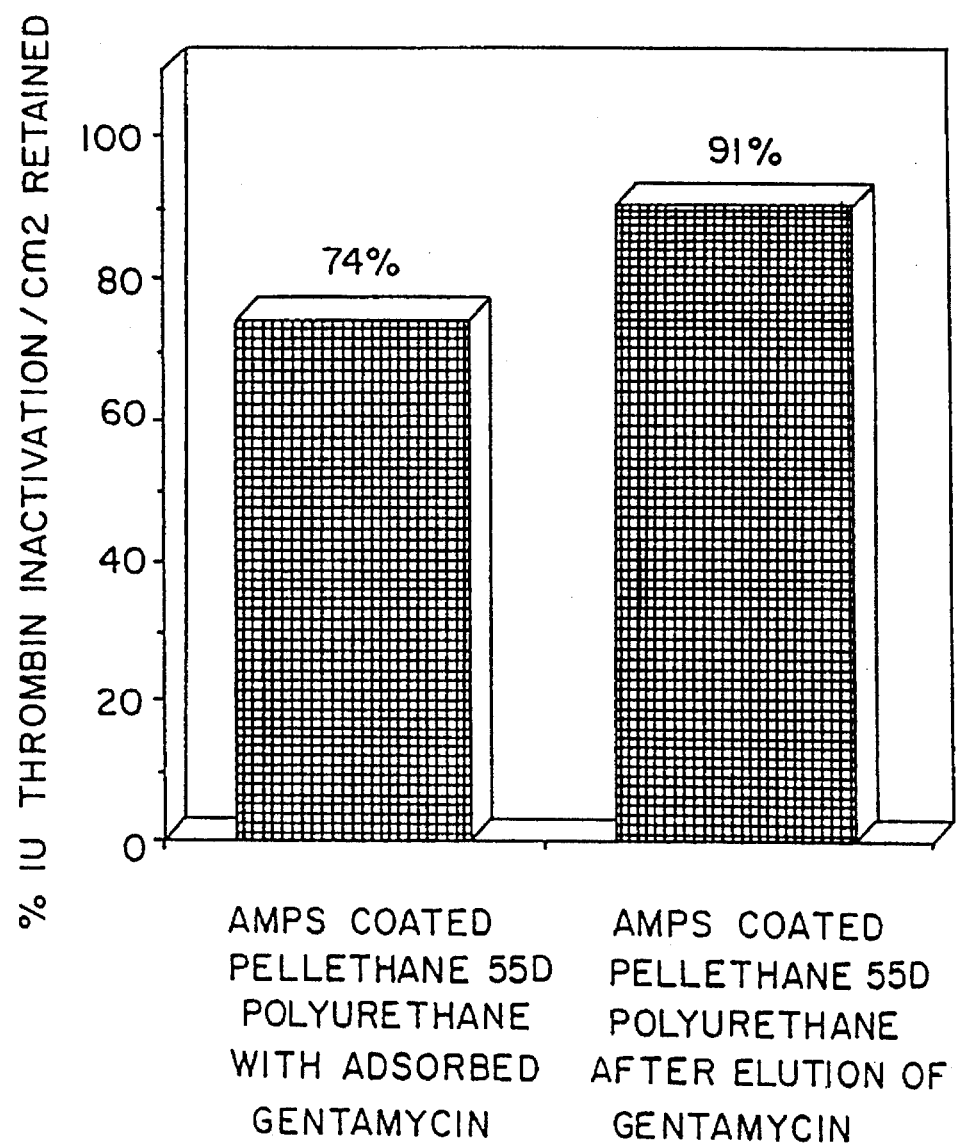
FIG. 5 is a graph showing ATIII activity of AMPS coated Peltethane 55D polyurethane containing gentamycin and AMPS coated Pellethane 55D polyurethane after 24 hour elution of gentamycin.

Samples were first rinsed in phosphate-buffered saline (PBS) for 15 minutes prior to ATIII exposure. Following rinsing, the samples were exposed for 15 minutes to an excess of purified ATIII (50 IU/ml). Non adsorbed ATIII was removed by rapid rinsing in tris-buffered saline, pH 7.4 at 25° C. (100 mM NaCl and 50 mM tris). The amount of surface bound and activated ATIII was then estimated by incubating the samples with an excess of thrombin. After a 10 minute incubation with constant mixing at 25° C., the residual thrombin was measured by reaction with a chromogenic substrate (H-D-phenylalanyl-L-pipecolyl-L-arginine-p-nitroanilide dichloride) in a spectrophotometer. The change in absorbance at 405 nm was then measured. The results are given in FIG. 5. As the results demonstrate, the AMPS surface which contains adsorbed gentamycin retains a large percentage (74%) of its original ATIII activity. The ATIII activity which the AMPS surface loses due to the adsorbed gentamycin returns upon the elution of the gentamycin. It is concluded, therefore, that the AMPS coating possesses most of its antithrombogenic properties while loaded with gentamycin and regains all of its antithrombogenic properties upon the elution of gentamycin. Therefore, such a coating is nonthrombogenic and bacterial resistant.

The idea behind the AMPS coating is to create a heparin-like surface to prevent thrombogenicity with the added benefit of providing slip properties to implantable devices. The data discussed above demonstrate that the coating does indeed create a heparin-like surface by virtue of this selective adsorption of ATIII. In addition to these antithrombogenic properties, it was discovered that the anionic AMPS coating has the ability to ionically bind and slowly release cationic antimicrobials thus imparting long-term bioactive properties to the surface as well. It was found that this addition of bioactive agents did not adversely affect the ability of the AMPS surface to selectively adsorb ATIII.

These results indicate that the AMPS coating is an effective nonthrombogenic as well as infection-resistant surface modifier significantly increasing the biocompatibility of implantable polymeric medical devices.

Other examples of cationic antimicrobials [attracted to (−) charged surfaces] are shown in Table 3 below.

TABLE 3

Gentamycin
Kanamycin
Neomycin
Silver ion
Chlorhexidine
Vancomycin
Streptomycin
Erythromycin Specific examples of anionic antimicrobials attracted to (+) charged surfaces] are shown in Table 4 below.

TABLE 4

Ampicillin
Oxacillin
Cefazolin
Bacitracin
Cephalosporin
Cephalothin
Cefuroxine
Cefoxitin
Norfloxacin
Perfloxacin
Sulfadiazine

BASIC FIBROBLAST GROWTH FACTOR BINDING TO IONICALLY CHARGED SURFACES (GRAFT POLYMER)

Basic fibroblast growth factor (bFGF) has been isolated from many tissue sources and is a single chain protein with an approximate molecular weight of 18,000. It is a cationic protein with an isoelectric point of 9. The binding of bFGF with ionically charged surfaces is demonstrated below.

Polyurethane samples used herein possessed either negatively charged, positively charged or neutrally charged hydrophilic graft polymer surfaces. The modified polyurethane surfaces were prepared via a ceric ion grafting. Non-coated polyurethane samples (PU) were also used.

EXAMPLE 5

Neutrally Charged Samples (AAm)

Neutrally charged polyurethane samples (1 cm$^2$) were prepared by placing the samples into the following degassed grafting solution for 45 minutes at room temperature.

50 g acrylamide (AAm)

1.1g ceric ammonium nitrate 1.3 g nitric acid 70 ml deionized (DI) water

Following grafting, the samples were rinsed thoroughly in DI water.

EXAMPLE 6

Positively Charged Samples (APMA) (AAm)

Positively charged polyurethane samples (1 cm$^2$) were prepared by placing the samples into the following degassed grafting solution for 45 minutes at room temperature.

40 g acrylamide (AAm)

10 g N-(3-aminopropyl)methacrylamide hydrochloride 1.1 g ceric ammonium nitrate 1.3 g nitric acid 70 ml DI water Following grafting, the samples were rinsed thoroughly in DI water.

EXAMPLE 7

Negatively Charged Samples (AMPS)

Negatively charged polyurethane samples (1 cm$^2$) were prepared via placing the samples into the following degassed grafting solution for 2 hours at room temperature.

50 g 2-acrylamido-2-methylpropane sulfonic acid (AMPS)

1.1 g ceric ammonium nitrate 1.3 g nitric acid 70 ml DI water

Following grafting, the samples were rinsed thoroughly in DI water.

RESULTS—EXAMPLE 5–7

The grafted samples (1 cm$^2$) were then placed into 24 well polystyrene tissue culture plates and secured in place with silicone rubber rings. The samples were stored hydrated in water at room temperature until assayed.

Diluted bFGF in phosphate buffered saline (PBS) with 1 mg/mL bovine serum albumin (BSA). Incubated samples overnight at 25° C. Three concentrations of bFGF were studied: 0.5 ng/mL, 5 ng/mL and 50 ng/mL. 0.1mg $^{125}$I-labeled bFGF were added to each well. 0.5 mL total volume per well. The samples were washed with PBS. The samples were counted in a Beckman gamma counter.

TABLE 5

RESULTS:

| Treatment: | CPM |
| --- | --- |
| PU (control) | 8971 |
| #5 AAm | 6721 |
| #6 APMA | 4113 |
| #7 AMPS | 29931 |

Figure 6:
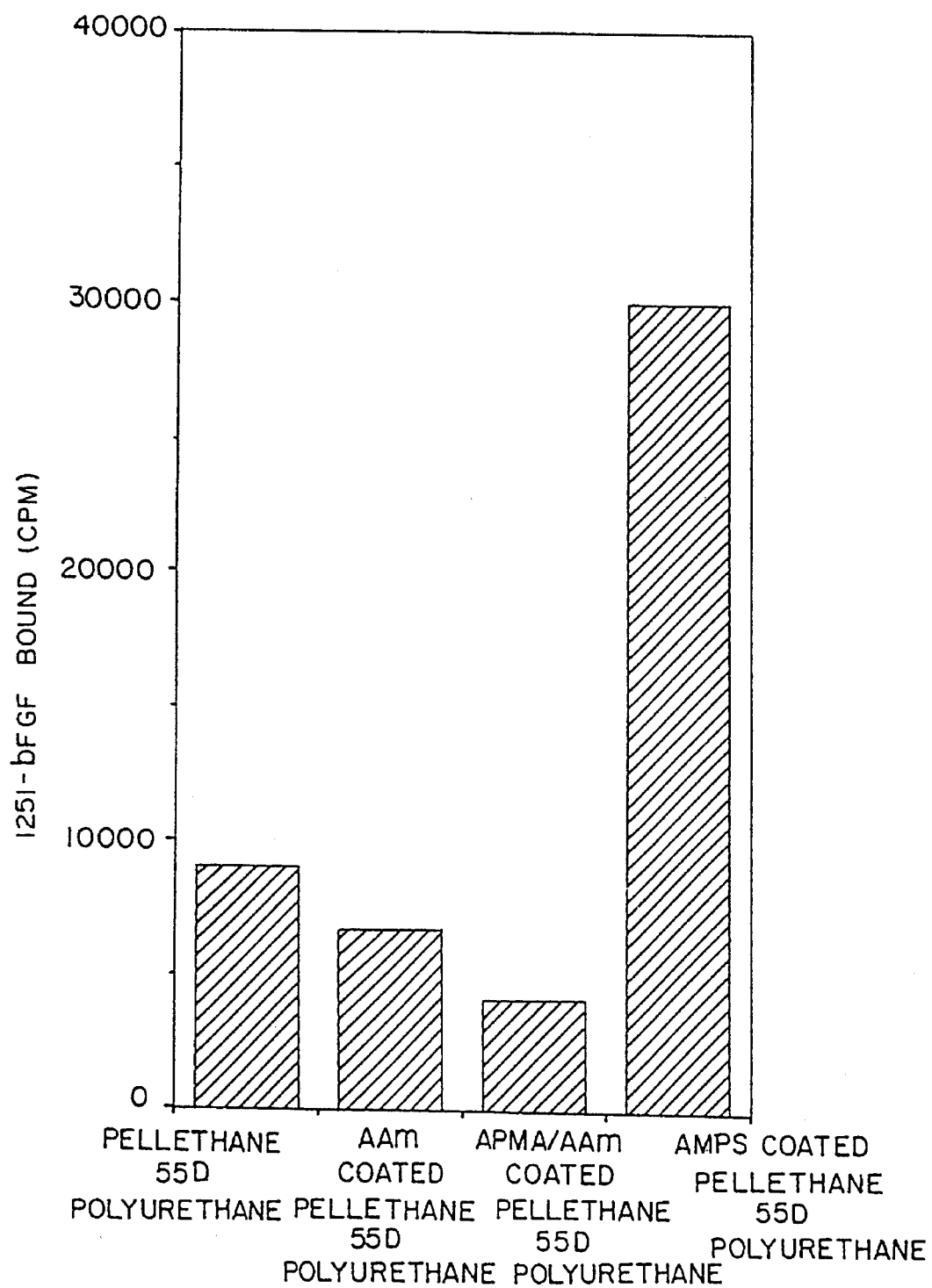
FIG. 6 is a graph showing the amount of fibroblast growth factor which binds to polyurethane (PU), and to polyurethane grafted with acrylamide (AAm), N-(3-aminopropyl) methacrylamide hydrochloride (APMA) and acrylamide (AAm) copolymer or 2-acrylamido-2-methylpropane sulfonic acid (AMPS).

As can be seen from the data in Table 5 and FIG. 6, the amount of fibroblast growth factor which binds to the various surfaces is demonstrated. As the results indicate the negatively charged samples (Amps) adsorbed considerably more bFGF than did the other samples.

Figure 7:
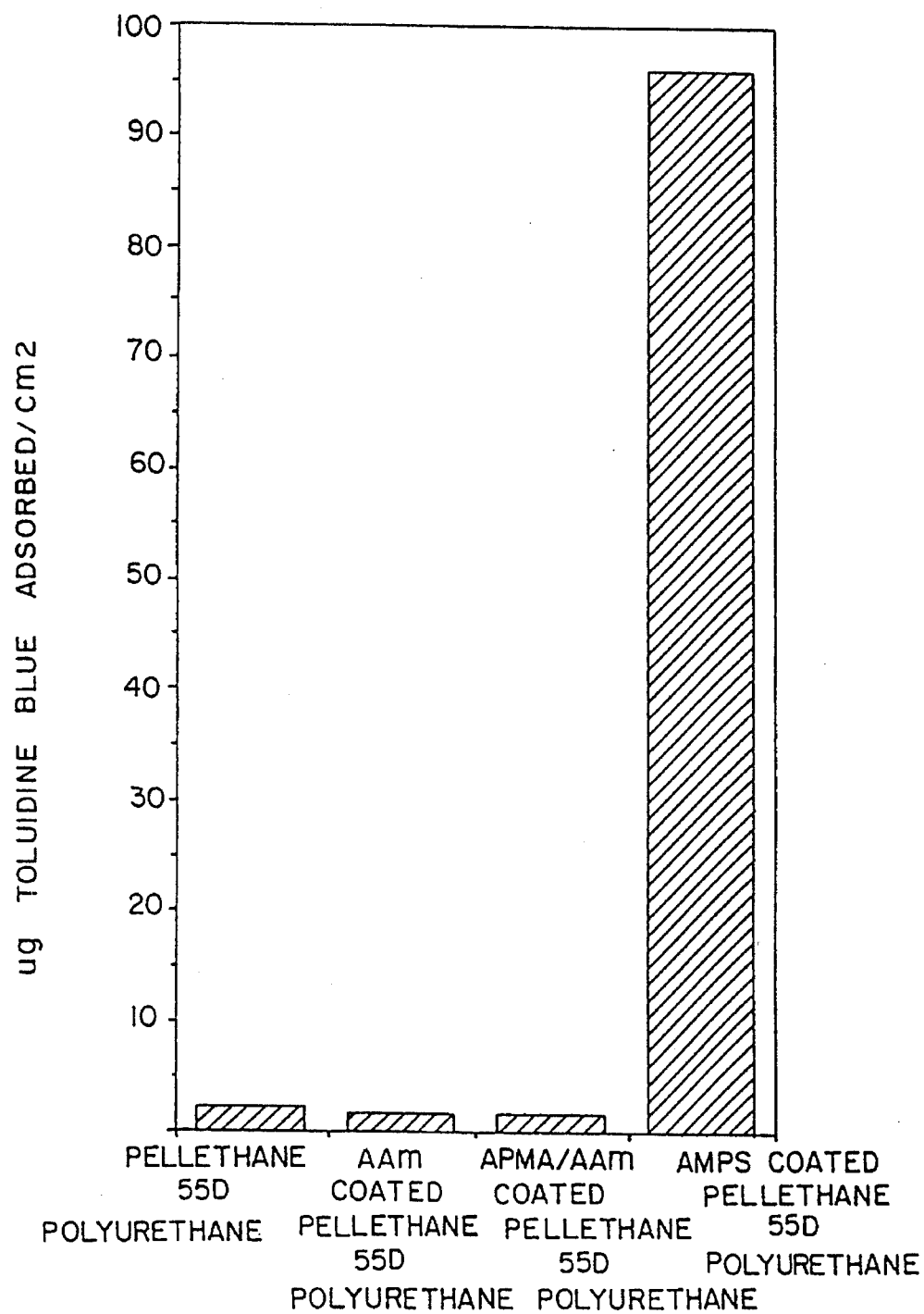
FIG. 7 is a graph showing toluidine blue dye adsorption for the same substrates as in FIG. 6 i.e., PU, AAm, APMA/AAm and AMPS.

On the other hand, if one wanted to achieve the opposite result i.e., repulsion as opposed to attraction; one would select a graft polymer/bioagent having similar charges (+,+) or (−,−). This might be done in those instances where one wishes to minimize any interaction therebetween. For example, one may wish to minimize peptide interaction with respect to an implanted surface. To accomplish this one may graft hydrophylic polymers on the implanted surface that contains similar charges to the peptide of interest thus enhancing the lack of interaction through charge repulsion. As an example, consider FIG. 6, in which one could select an APMA/AAm coating to repulse bFGF. Consider FIG. 7 in which one could select an APMA/AAm coating to repulse toluidine blue. Lastly consider FIG. 8 in which one could select an AMPS coating to repulse Ponceau S.

IONIC BINDING OF DYES TO CHARGED SURFACES (GRAFT POLYMER)

The ability of a cationic and an anionic dye to bind to charged surfaces was also investigated. This is of interest because of the concept of utilizing various dyes as biological ligands. The cationic dye used in this study was Toluidine Blue dye and the anionic dye used was Ponceau S dye.

Polyurethane substrate samples used herein possessed either negatively charged, positively charged or neutrally charged hydrophilic surfaces. The polyurethane surfaces were prepared via a ceric ion grafting. Uncoated polyurethane samples (PU) were also used.

EXAMPLE 8

Neutrally Charged Samples (AAm)

Neutrally charged polyurethane samples (1 cm$^2$) were prepared via placing the samples into the following degassed grafting solution for 45 minutes at room temperature.

50 g acrylamide (AAm)

1.1 g ceric ammonium nitrate 1.3 g nitric acid 70 ml deionized DI water

Following grafting, the samples were rinsed thoroughly in DI water.

EXAMPLE 9

Positively Charged Samples (APMA/AAm)

Positively charged polyurethane samples (1 cm$^2$) were prepared via placing the samples into the following degassed grafting solution for 45 minutes at room temperature.

40 g acrylamide (AAm)

10 g N-(3-aminopropyl)methacrylamide hydrochloride (APMA)

1.1 g ceric ammonium nitrate 1.3 g nitric acid 70 ml DI water

Following grafting, the samples were rinsed thoroughly in DI water.

EXAMPLE 10

Negatively Charged Samples (AMPS)

Negatively charged polyurethane samples (1 cm$^2$) were prepared via placing the samples into the following degassed grafting solution for 2 hours at room temperature.

50 g 2-acrylamido-2-methylpropane sulfonic acid (AMPS)

1.1 g ceric ammonium nitrate 1.3 g nitric acid 70 ml DI water

Following grafting, the samples were rinsed thoroughly in DI water.

RESULTS—EXAMPLES 8–10

Grafted samples of Examples 8–10 (1 cm$^2$) were placed into either a 1% Toluidine Blue dye in DI water solution (12a–14a) or a 1% Ponceau S dye in DI water solution (12b–14b) for 1 minute. Following dyeing the samples were rinsed thoroughly in 500 ml DI water. Dyed samples were agitated in a 1% sodium dodecyl sulfate (SDS) in DI water solution for 24 hours.

The absorbance of each SDS sample solution containing eluted dye was then measured on a Beckman DU 64 spectrophotometer at a wavelength of 640 nm for Toluidine Blue dye and 520 nm for Ponceau S dye.

The amount of dye adsorbed to each sample is then calculated by comparing the sample absorbance to an absorbance standard curve generated using known amounts of dye. The results for Toluidine blue dye adsorbance are shown in Table 6, as well as FIG. 7.

TABLE 6

Toluidine Blue Dye Adsorbance

| Treatment: | mg Toluidine Blue Adsorbed/cm$^2$ |
|---|---|
| PU (Control) | 2.17 |
| #8a AAm | 1.52 |
| #9a APMA/AAm | 1.58 |
| #10a AMPS | 96.07 |

Figure 8:
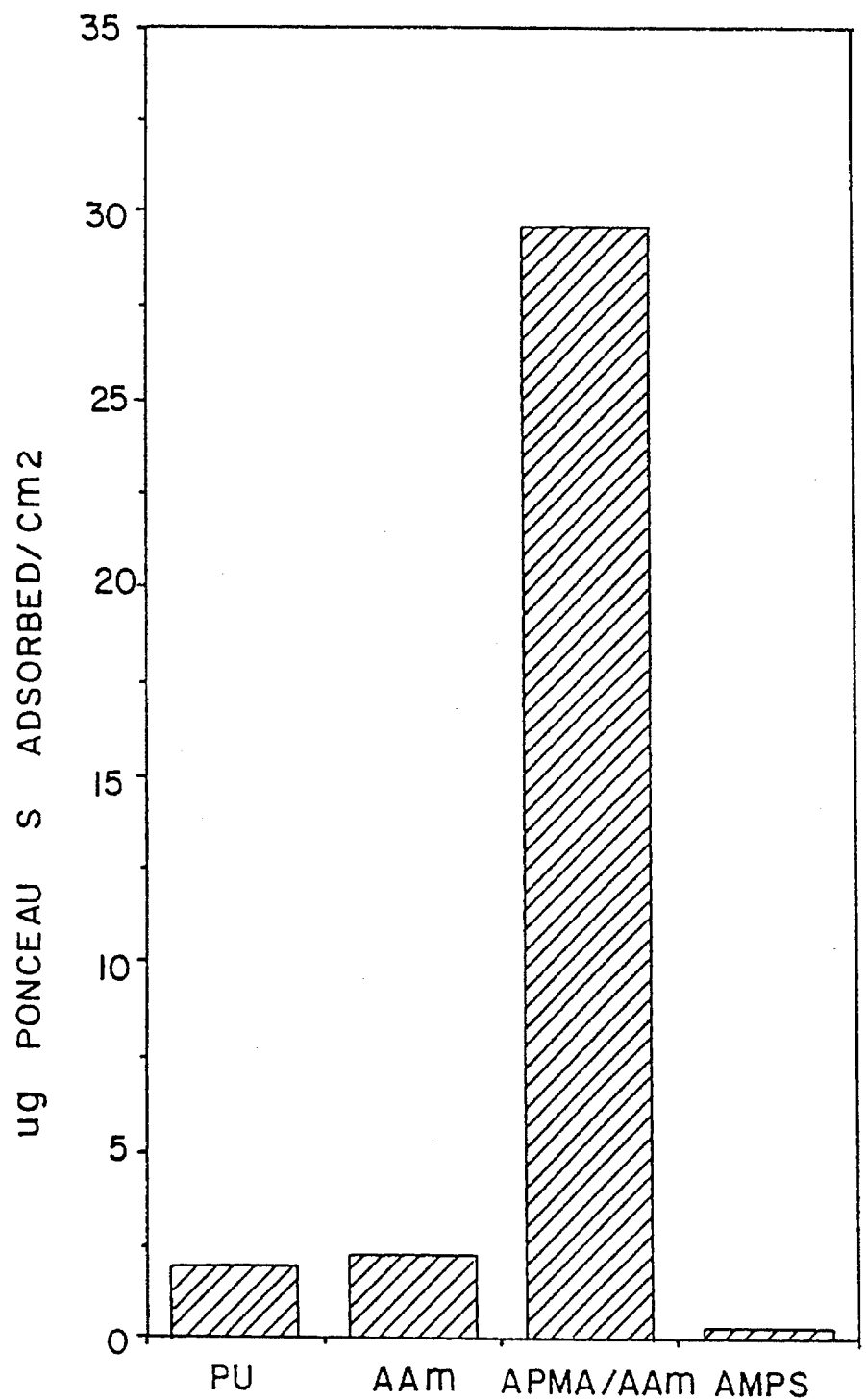
FIG. 8 is a graph showing the binding of Ponceau S dye to the same substrates as in FIG. 6 and FIG. 7 i.e., PU, AAm, APMA/AAm and AMPS.

Similar results are shown in Table 7 and FIG. 8 for Ponceau S dye adsorbance.

TABLE 7

Ponceau S dye Adsorbance

| Treatment: | mg Ponceau S Absorbed/cm$^2$ |
|---|---|
| PU (Control) | 1.90 |
| #8b AAm | 2.24 |
| #9b APMA/AAm | 29.62 |
| #10b AMPS | 0.24 |

As the results indicate, the negatively charged samples (AMPS) adsorbed considerably more of the cationic dye (Toluidine Blue) than did the other samples. Whereas, the positively charged samples (APMA/AAm) adsorbed considerably more of the anionic dye (Ponceau S) than did the other samples.

COVALENT BINDING OF BIOACTIVE AGENTS

The concept of covalently binding bioactive agents such as dyes onto implantable materials, such as polyurethane, having grafted slip coatings is another aspect of this invention. Materials which have surfaces that preferentially bind albumin will be less thrombogenic, less pro-inflammatory and less liable to harbor adherent pathogenic bacteria.

The present invention describes herein techniques for covalently attaching Blue Dextran, dextran or Cibacron Blue dye to a grafted polymer surface. The binding of these agents is based on the generation of free radicals on a base material surface and the copolymerization of vinyl monomers directly to that surface followed by covalent attachment of bioactive agents i.e., Blue Dextran, dextran or Cibacron Blue dye. A number of techniques have been reported in the area of graft copolymerization on materials. Graft copolymerization provides a method of controlling the composition of the grafted polymer by varying monomers and varying their concentrations, it is possible to create grafted surfaces that possess the following properties.

1. Hydrophilicity.
2. No non-specific interactions with proteins in general.
3. A sufficient number of active groups that are amenable to the chemical functionalization and modification required in covalently attaching bioactive agents e.g., Blue Dextran, dextran or Cibacron Blue dye.
4. Mechanical, chemical and enzymatic stability.

Grafting can be engineered stoichiometrically to produce surfaces containing the desired amount of hydrophilicity and the desired amount of functional groups used for coupling the bioactive agents. Hydrophilic spacer monomers (neutral, anionic and cationic) can be selected to produce appropriately charged hydrophilic spacers. Coupling monomers can be selected based on pendant functional groups, i.e., —OH, —NH$_2$, —CHO, —NCO, needed or wanted for immobilizing a bioactive agent e.g., Blue Dextran, Dextran or Cibacron Blue dye.

Graft copolymerizations onto poly(ether urethane) with CeIV ion has been the mechanism utilized. The monomers utilized are acrylamide (AAm) and N-(3-aminopropyl) methacrylamide hydrochloride (APMA). These monomers were chosen based partly on their reactivity and water solubility characteristics. The AAm monomer is used as the hydrophilic spacer monomer. The APMA monomer is used as the coupling monomer. AAm has been used extensively as an affinity chromatographic matrix. AAm is a neutral hydrophilic monomer; therefore, polymers of AAm have shown little protein association. APMA is an amino containing monomer, thus allowing the attachment of Blue Dextran, dextran or Cibacron Blue dye.

Cibacron Blue dye can be reacted directly to the amino functional group on the APMA monomer through its reactive chlorine on its triazine ring. Dextran and Blue Dextran can be covalently attached to the amine group on the APMA through a stabilized Schiff base reaction. The dextran or Blue Dextran is first oxidized using sodium periodate. The oxidation forms reactive aldehyde groups which react with the primary amines on APMA forming imines. The imines are stabilized using sodium cyanoborohydride.

Cibacron Blue dye can be reacted to the covalently attached dextran forming Blue Dextran on the surface of the material. This gives the ability of attaching as much dye as desired on to the surface. Also, the dextran that is attached can be varied in molecular weight as desired.

BLUE DEXTRAN SURFACE COATING TECHNIQUE

Figure 9A:
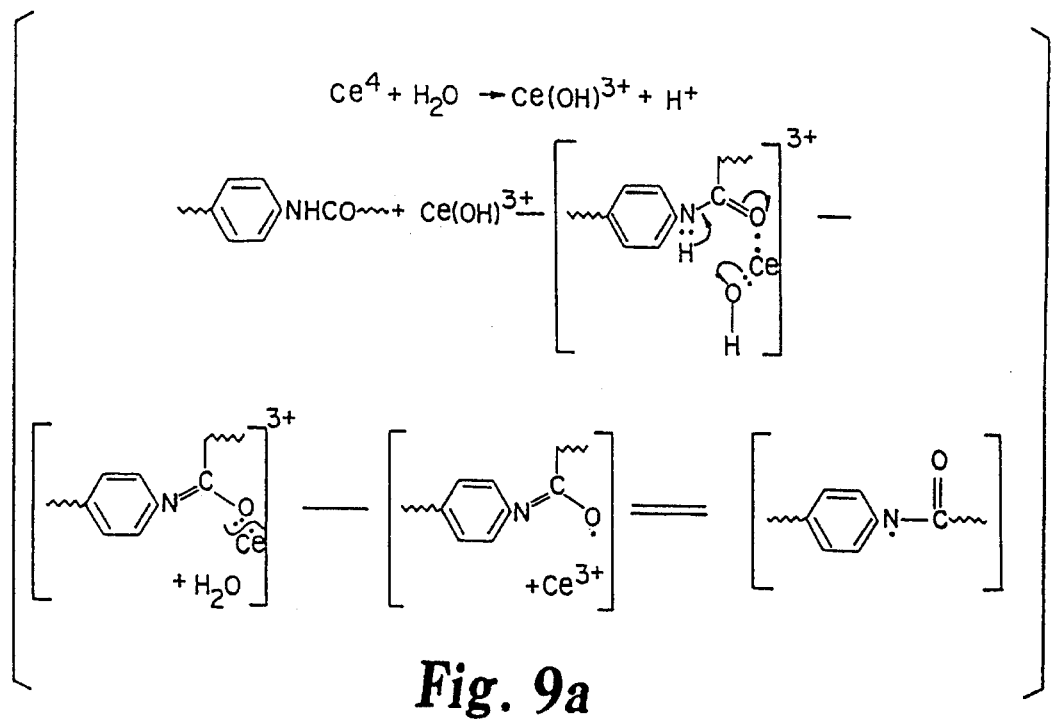
FIG. 9a shows the proposed reactive mechanism of CeIV ion initiation of free radicals on a polyurethane surface.
Figure 10:
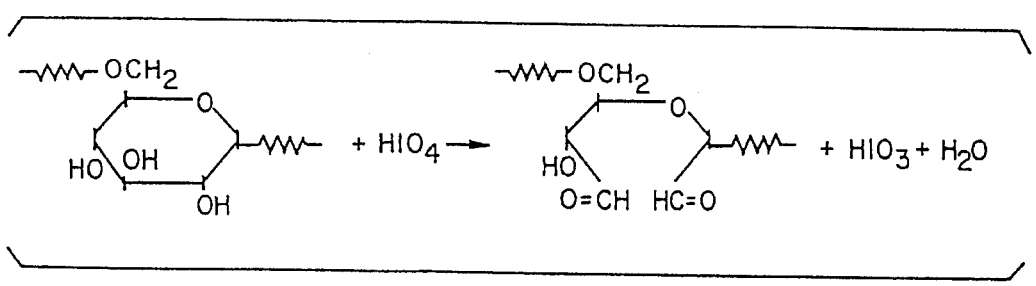
FIG. 10 shows the periodate oxidation of dextran.
Figure 11:
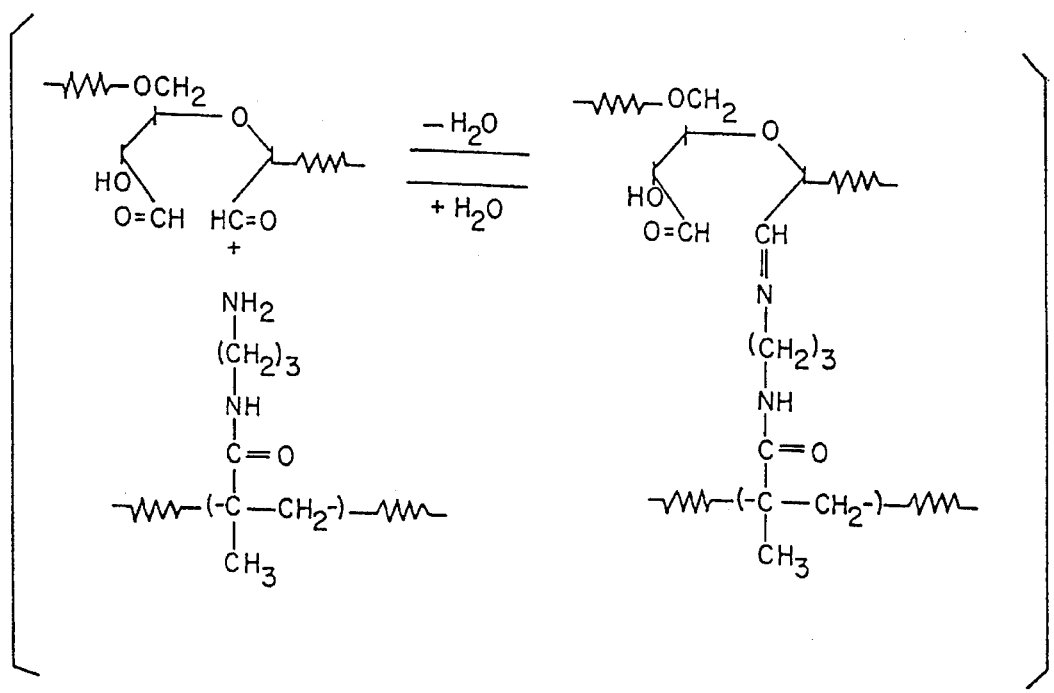
FIG. 11 shows the reductive amination (Shiff base reaction) of oxidized dextran and grafted APMA.
Figure 12:
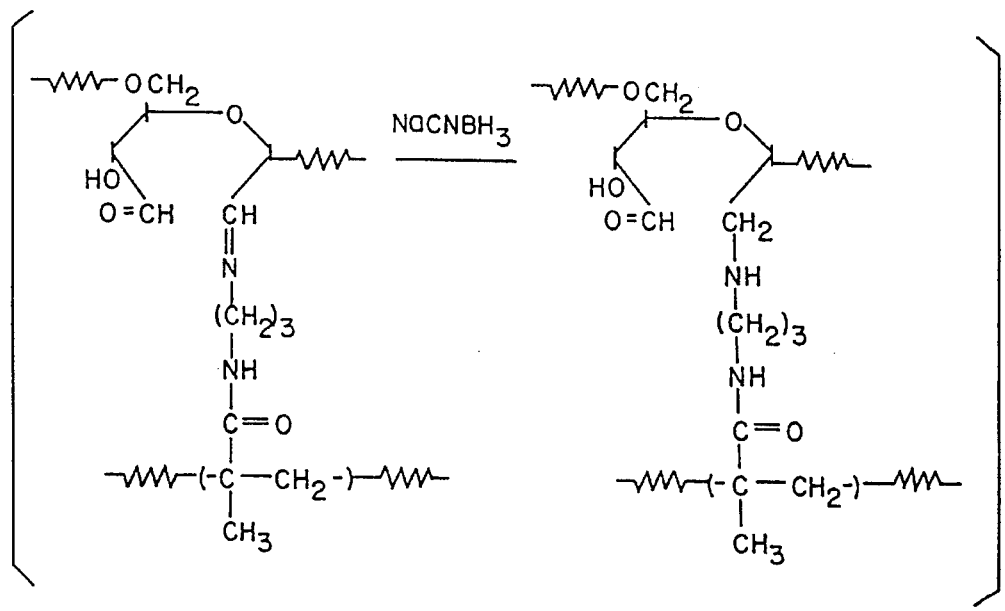
FIG. 12 shows the sodium cyanoborohydride stabilization of imine linkage.
Figure 13:
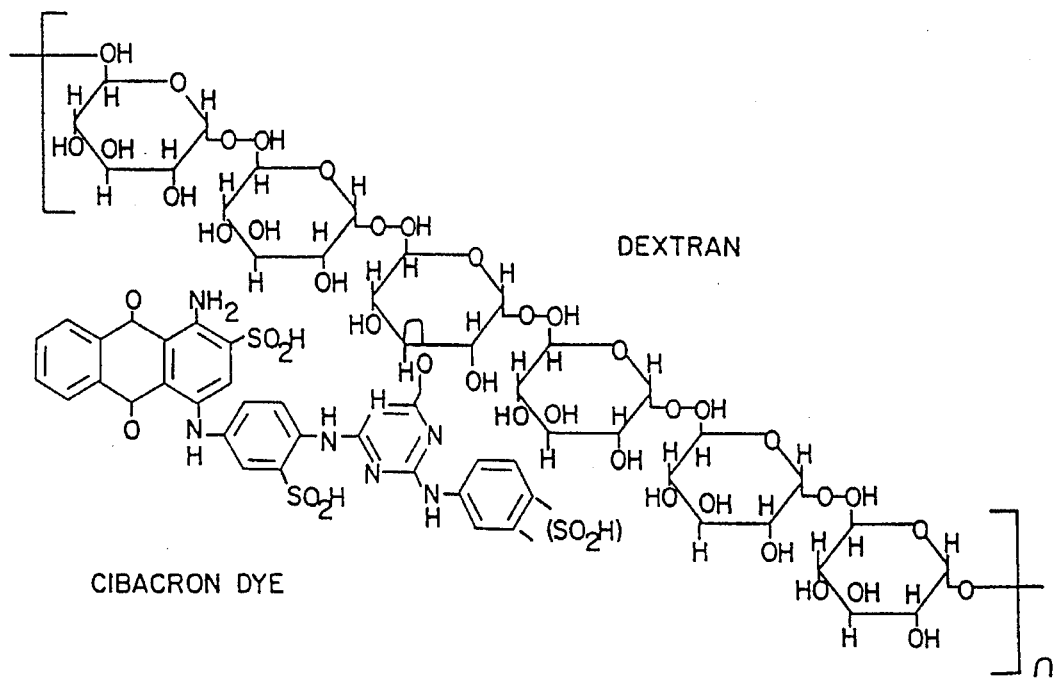
FIG. 13 shows covalently coupled Cibacron Blue dye to surface bound dextran.

The Blue Dextran surface-derivatization technique begins with the graft copolymerization of AAm and APMA monomers onto a clean polyurethane surface with CeIV ion. The CeIV ion creates a free radical on the polyurethane surface which initiates the graft copolymerization of the acrylamides (FIGS. 9a and b). The APMA monomer contains a primary amino group that is then used for coupling Dextran which is later dyed with Cibacron Blue dye. The attachment of Dextran consists of first oxidizing the carbohydrate with sodium periodate thus forming aldehyde groups (FIG. 10). These aldehyde groups are then covalently attached to the primary amino group on the grafted APMA monomer through reductive amination (Schiff base reaction) (FIG. 11). Sodium cyanoborohydride (NaCNBH$_3$) is used to stabilize the imine linkage (FIG. 12). Finally, Cibacron Blue dye is then covalently coupled to the surface-bound dextran (FIG. 13).

The amount of surface amination (the graft copolymerization of APMA and AAm) that takes place on the polyurethane surface can be effected via monomer concentrations, catalyst concentration, and grafting time. Therefore, a study was performed to determine the optimum grafting conditions for achieving a highly aminated polyurethane surface. The amount of surface amination achieved is measured via staining the surface with Ponceau S dye, a negatively charged dye molecule. The dye ionically associates with primary amines on the aminated surface. After staining, the dye is released from the surface using SDS and quantified spectrophotometrically at 520 nm.

EXAMPLE 11

APMA/AAm Grafting Procedure

Extruded Pellethane 55D films were extracted in acetone and ethanol prior to CeIV ion grafting. The solvent extraction process removes any processing aides that could interfere with the grafting process. Monomer solutions in DI water were prepared and various amounts of CeIV ion solution were added. The CeIV ion solution consisted of 2.74 g. ceric ammonium nitrate and 3.15 g. nitric acid in 50 ml DI water. The CeIV—monomer solutions were degassed and released to nitrogen prior to grafting. Pelletbane samples were placed into the degassed monomer solutions and stirred. Grafting was allowed to proceed for various amounts of time. Samples were then removed and thoroughly washed in DI water.

The amount of surface amination that took place upon graft copolymerization of the samples was measured using Ponceau S dye. Grafted samples were placed into a 1% Ponceau S dye/DI water solution for 1 minute and then rinsed in DI water. The bound dye was then released from the surface using a 1% SDS solution. The amount of dye eluted was determined spectrophotometrically at 520 nm.

Table 8 describes the various grafting conditions employed and the amount of surface amination achieved as determined by the Ponceau S staining technique. Based on these results samples were grafted using a total monomer concentration of 50%, a reaction time of 30 minutes, a catalyst concentration of 20% and an AMPA/AAm monomer ratio of 0.10. (10/90%).

EXAMPLE 12

Dextran Attachment to Aminated Polyurethane Surfaces

Dextran was first oxidized by placing 1.0 g in 18 g DI water containing 1.0 mg NaIO$_4$. The mixture was incubated in the dark for 2 hours. The oxidized mixture was then dialyzed against DI water for 24 hours to remove any excess periodate. APMA/AAm grafted Pellethane 55D samples were then placed into the oxidized dextran solution for one hour at room temperature followed by the addition of NaCNBH$_3$ (3 mg/ml). The resultant mixture was allowed to react for 2 hours at room temperature. The samples were then removed and rinsed thoroughly in DI water.

EXAMPLE 13

Samples containing covalently coupled dextran were then dyed with Cibacron Blue dye.

Samples were placed into a dye solution consisting of 1.0 g Cibacron Blue dye, 4.0 g NaCl, 12.0 g NaHCO$_3$ in 200 ml DI water overnight. Blue Dextran samples were then thoroughly rinsed in DI water.

SEM Analysis of Blue Dextran Surface-Coated Material (Example 13)

Scanning electron microscopy was performed on surfaces of Blue Dextran surface-coated Pellethane 55D. The surfaces were investigated at a magnification of 6000X. SEM photographs of the surface indicate the Blue Dextran/APMA/AAm coating appears to be approximately 2 microns thick and uniformly distributed on the surface.

TABLE 8

Surface Amination of Pellethane 55D Films.

| Monomer | Rxn Time | Catalyst % | APMA/AAM | Ponceau S Abs. |
|---|---|---|---|---|
| 50 | 30 | 20 | 0.10 | 0.911 |
| 50 | 30 | 10 | 0.10 | 0.770 |
| 50 | 30 | 40 | 0.10 | 0.655 |
| 50 | 30 | 5 | 0.10 | 0.547 |
| 50 | 30 | 60 | 0.10 | 0.516 |
| 50 | 30 | 3 | 0.10 | 0.084 |
| 50 | 30 | 1 | 0.10 | 0.004 |
| 50 | 15 | 20 | 0.10 | 0.590 |
| 50 | 15 | 60 | 0.10 | 0.395 |
| 50 | 15 | 10 | 0.10 | 0.368 |
| 50 | 15 | 5 | 0.10 | 0.331 |
| 50 | 15 | 40 | 0.10 | 0.300 |
| 50 | 15 | 3 | 0.10 | 0.075 |
| 50 | 15 | 1 | 0.10 | 0.006 |
| 50 | 5 | 20 | 0.10 | 0.150 |
| 50 | 5 | 60 | 0.10 | 0.144 |
| 50 | 5 | 40 | 0.10 | 0.137 |
| 50 | 5 | 10 | 0.10 | 0.109 |
| 50 | 5 | 5 | 0.10 | 0.041 |
| 50 | 5 | 3 | 0.10 | 0.010 |
| 50 | 5 | 1 | 0.10 | 0.006 |
| 40 | 15 | 3 | 0.05 | 0.367 |
| 40 | 15 | 5 | 0.05 | 0.363 |
| 40 | 15 | 1 | 0.05 | 0.017 |
| 30 | 15 | 3 | 0.05 | 0.310 |
| 30 | 15 | 5 | 0.05 | 0.232 |
| 30 | 15 | 1 | 0.05 | 0.030 |
| 20 | 15 | 3 | 0.05 | 0.328 |
| 20 | 15 | 5 | 0.05 | 0.217 |
| 20 | 15 | 1 | 0.01 | 0.091 |
| 20 | 5 | 3 | 0.05 | 0.060 |
| 20 | 5 | 1 | 0.05 | 0.041 |

ESCA Analysis of Blue Dextran Surface-Coated Material

ESCA was done on uncoated Pellethane 55D samples (control), APMA/AAm surface-coated Pelletbane 55D samples, Dextran surface-coated Pellethane 55D samples and Blue Dextran surface-coated Pelletbane 55D samples (Table 9). As the results indicate, Blue Dextran is present on the Blue Dextran surface-coated material's surface. This is demonstrated by the decrease in carbon, an increase in oxygen and an increase in sulfur.

TABLE 9

ESCA analysis of Blue Dextran surface-coated 55D (Blue Dextran), Dextran surface-coated 55D (Dextran), APMA/AAm surface-coated 55D (APMA/AAm) and uncoated Pellethane 55D (55D). Theoretical percentages are also given for Blue Dextran (1 dye/10 sugars).

| SAMPLE | % CARBON | % OXYGEN | % NITROGEN | % SULFUR |
|---|---|---|---|---|
| 55D (control) | 78.50 | 15.90 | 3.90 | 0.00 |
| #11 APMA/AAm | 67.84 | 19.70 | 12.46 | 0.00 |
| #12 Dextran | 66.16 | 20.21 | 13.63 | 0.00 |
| #13 Blue Dextran | 62.36 | 20.76 | 12.91 | 1.43 |
| $BD_{theoretical}$ | 52.80 | 40.99 | 4.35 | 1.86 |

Tensile Properties of Blue Dextran Surface-Coated Material

Tensile properties of Blue Dextran surface-coated Pellethane 55D films, dextran surface-derivatized Pellethane 55D films, APMA/AAm surface-derivatized Pelletbane 55D films and Pelletbane 55D films were measured using an Instron mechanical testing apparatus. As shown in Table 10, the graft copolymerization step and further derivatization steps of the Blue Dextran surface derivatization technique do not substantially alter the physical properties of the polyurethane.

TABLE 10

Tensile Properties of Blue Dextran surface-coated Pellethane 55D, Dextran surface-coated Pellethane 55D, APMA/AAm surface-coated Pellethane 55D and uncoated Pellethane 55D films.

| SAMPLE | UTS (psi) | % ELONGATION |
|---|---|---|
| 55D | 7570 ± 1440 | 361 ± 35 |
| #11 APMA/AAm | 7950 ± 736 | 444 ± 37 |
| #12 Dextran | 7031 ± 634 | 438 ± 38 |
| #13 Blue Dextran | 6806 ± 875 | 390 ± 40 |

EXAMPLE 14

The Adsorption of Albumin on Surface-Coated Material

Figure 14:
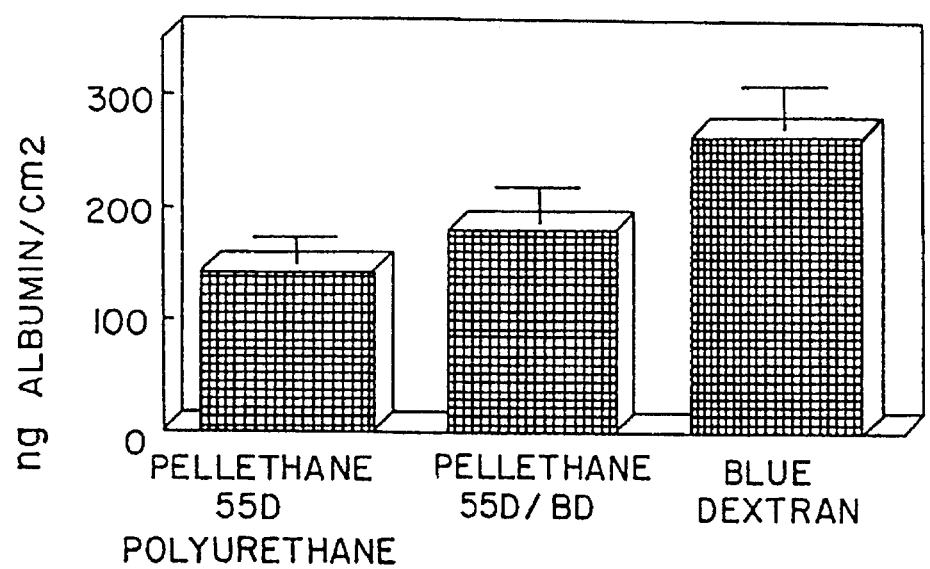
FIG. 14 is a graph showing $^{125}$I-Albumin adsorption to Pollethane 55D polyurethane, Blue Dextran bulk derivatized Pellethane 55D polyurethane (55D/BD) and Blue Dextran surface derivatized Pellethane 55D polyurethane (Blue Dextran).

The extent of binding of radiolabeled albumin to Blue Dextran surface-coated samples, Blue Dextran bulk-loaded samples (55D/BD) and Pelletbane 55D samples (control) were studied. The samples were rinsed in phosphate buffered saline (PBS) for 15 minutes each prior to incubation in $^{125}$I-albumin (0.08 mg/ml) for 15 minutes. The samples were then removed and washed again in PBS and counted in a scintillation counter. The results (FIG. 14) indicate that the Blue Dextran surface-coated samples adsorbed more albumin than the control 55D samples and more than the bulk incorporated 55D/BD samples.

EXAMPLE 15

The Adsorption of Albumin on the Surface-Coated Blue Dextran

Figure 15:
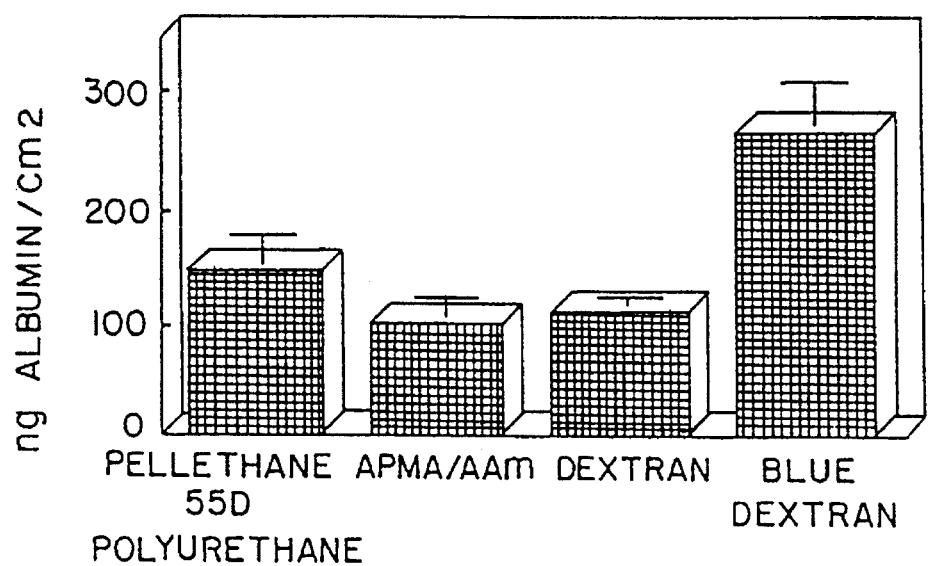
FIG. 15 is a graph showing $^{125}$I-Albumin adsorption to uncoated Pellethane 55D polyurethane, APMA/AAm surface-coated Pellethane 55D polyurethane, Dextran surface-coated 55D polyurethane and Blue Dextran surface-coated Pelletbane 55D polyurethane.

The extent of binding of radiolabeled albumin to Blue Dextran surface-coated samples, Dextran surface-coated samples, APMA/AAm surface-coated samples, and uncoated 55D samples was studied. This study was performed to determine if the binding of albumin was due to the presence of Cibacron Blue dye in the Blue Dextran coating or instead to the underlying dextran or APMA/AAm coatings. Samples were rinsed in PBS for 15 minutes each prior to incubation in $^{125}$I-albumin (0.08 mg/ml) for 15 minutes. The samples were then removed and washed again in PBS and counted in a scintillation counter. The results (FIG. 15) indicate that the Blue Dextran surface-coated samples adsorbed considerably more albumin than the other samples. This increase in albumin adsorption is therefore due to the presence of the Cibacron Blue dye in the Blue Dextran coating.

EXAMPLE 16

Immunogold Assay of Albumin Adsorbed to Surface-Coated Material

Figure 16:
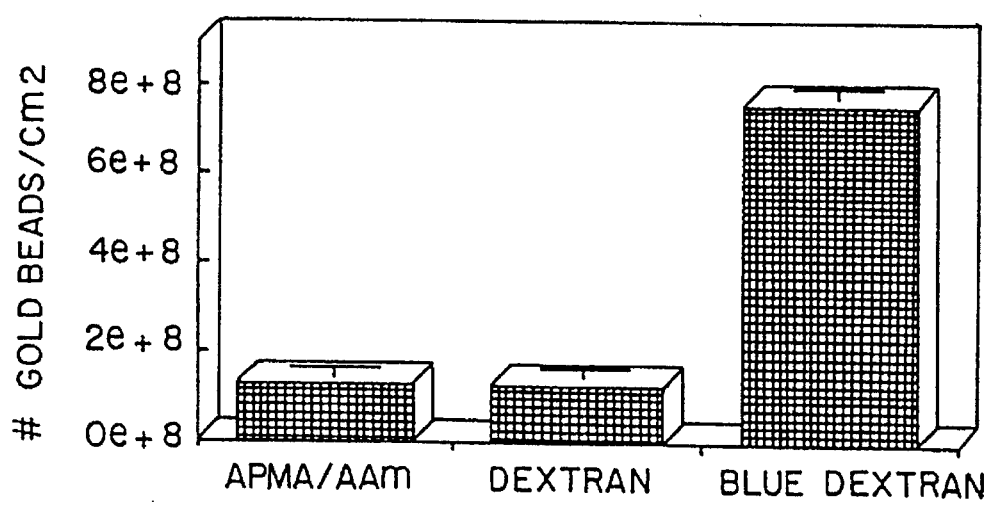
FIG. 16 is a graph showing Immunogold assay of albumin adsorved to APMA/AAm surface-coated Pellethane 55D polyurethane, dextran surface-coated Pellethane 55D polyurethane and Blue Dextran surface-coated Pellethane 55D polyurethane samples from fresh human plasma. Results are expressed as the number of gold beads/cm$^2$.

Another study was performed to determine if the binding of albumin was again due to the presence of Cibacron Blue dye in the Blue Dextran coating or instead to the underlying dextran or APMA/AAm coatings. In this study, samples were rinsed in PBS for 15 minutes each prior to incubation in fresh human plasma for 45 minutes at 37° C. Samples were then rinsed in PBS for 5 minutes. Following rinsing, the samples were placed into a 1.0% glutaraldehyde solution for 7 minutes and then rinsed in PBS for i0 minutes. Samples were then placed into 1 ml of 50 mM glycine solution for 7 minutes. The samples were then rinsed again in PBS for 10 minutes. Following rinsing, the samples were incubated in 1 ml of 15% milk solution containing 10 ug of Protein A solution for 1 hour at 37° C. Samples were then rinsed in PBS for 10 minutes. Following rinsing, the samples were placed in 0.5 ml of rabbit antihuman albumin and incubated for 1 hour at 37° C. Samples were then rinsed in PBS for 10 minutes. Following rinsing, the samples were incubated overnight in 1 ml of 2.5% glutaraldehyde solution at 4° C. After incubation in the glutaraldehyde solution the samples were rinsed in PBS for 10 minutes. Samples were then placed in 1 ml of 50 mM glycine solution for 25 minutes followed by a 1 hour incubation in 0.5 ml of gold labeled protein A solution at 37° C. Samples were then rinsed in PBS for 10 minutes and DI water for 10 minutes. Silver enhancement solution (0.5 ml) was then added to the samples for 15 minutes. Samples were removed and their surfaces were photographed with a scanning electron microscope. The number of beads on the SEM photos of the surfaces of APMA/AAm surface-derivatized 55D, dextran surface-derivatized 55D and the Blue Dextran surface-derivatized 55D were counted and tabulated in FIG. 16.

As the results indicate there is not a significant difference between dextran and APMA/AAm surfaces; however, there is significantly more albumin on Blue Dextran surfaces.

EXAMPLE 17

Drying and Rehydration Effects on Albumin Binding

Figure 17:
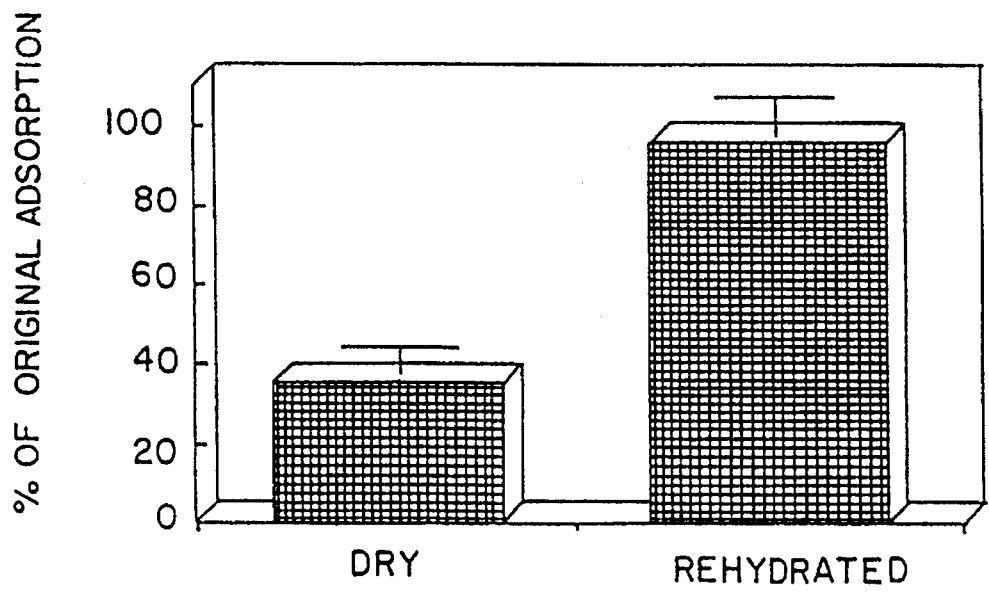
FIG. 17 is a graph showing $^{125}$I-Albumin adsorption to Blue Dextran surface-coated Pellethane 55D polyurethane samples dried and rehydrated in PBS for 1 hour. Results expressed as % of original albumin adsorption.

There were some concerns that, if the Blue Dextran Surface dried out, it might lose some of its albumin binding activity since the surface is extremely hydrophilic. Therefore, dehydration/rehydration studies were run. Blue Dextran surface-coated Pellethane 55D samples were dried out in an oven at 50° C. and then tested for albumin adsorption. Some of the dried samples were rehydrated in PBS for one hour and then tested for albumin adsorption. Albumin adsorption tests consisted of incubation of samples in $^{125}$I-albumin (0.08 mb/m.) for 15 minutes followed by rinsing in PBS and counting in a scintillation counter. As the results in FIG. 17 indicate drying out of the surface decreases its albumin activity, however, rehydration of dried samples appears to revive them.

EXAMPLE 18

The Selective Binding of Albumin by Surface-Coated Material

Figure 18:
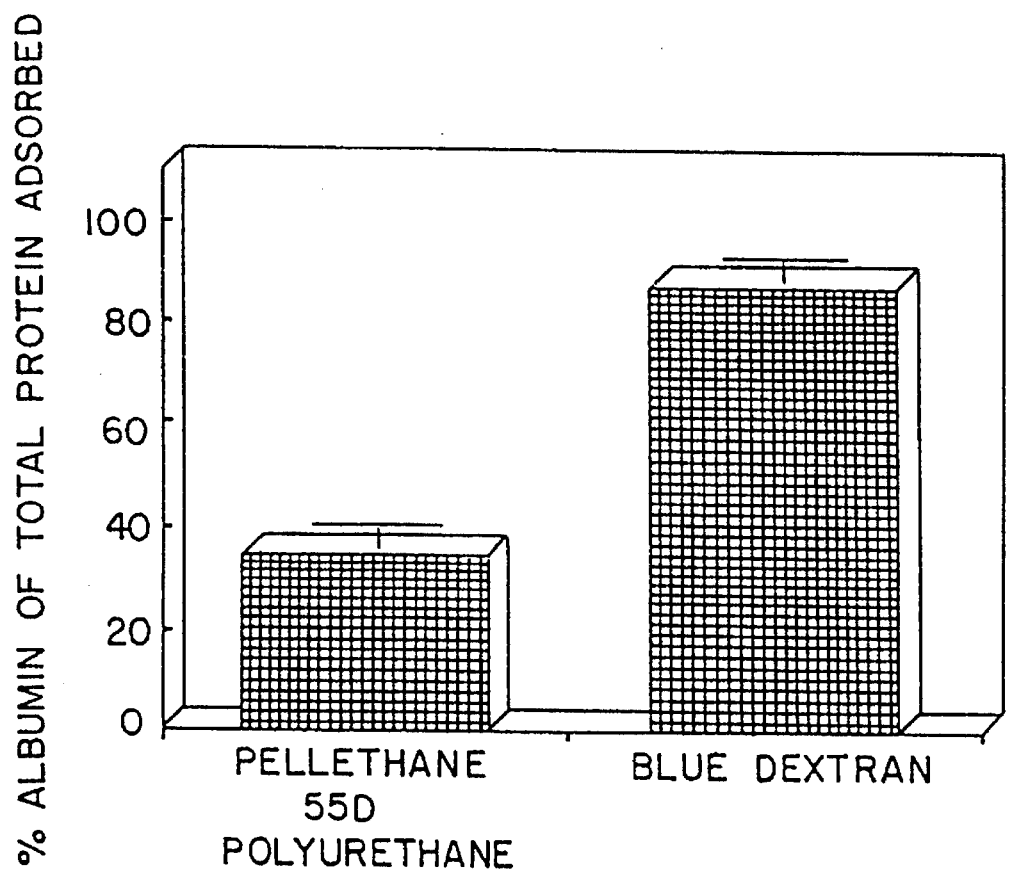
FIG. 18 is a graph showing the selective adsorption of albumin in the presence of fibrinogen to Pellethane 55D polyurethane and Blue Dextran surface-coated Pelletbane 55D polyurethane samples. Results are expressed as the % of total protein adsorbed to the surface which is albumin.

The selective binding of albumin to grafted Blue Dextran surfaces in the presence of fibrinogen was determined next using 50/50 mixtures of albumin/$^{125}$I-fibrinogen and $^{125}$I-albumin/fibrinogen. Fibrinogen was present to determine the nonspecific binding of proteins to the surface and because surfaces which avidly adsorb fibrinogen may be highly thrombogenic. Therefore, samples were exposed to an albumin/$^{125}$I-fibrinogen or $^{125}$I-albumin/fibrinogen mixture for 15 minutes and then rinsed with PBS. After the PBS rinsing, the samples were counted in a scintillation counter. As shown in FIG. 18, the Blue Dextran surface-coated samples had a greater ability to selectively adsorb albumin despite the presence of fibrinogen. The reversibility of albumin adsorbed to Blue Dextran surface-coated material was tested next.

EXAMPLE 19

The Reversible Binding of Albumin to Surface-Coated Material

The reversible binding of albumin was determined by studying its elutability with a 1% SDS wash. Protein that remains adherent to a surface following a SDS wash is considered denatured and irreversibly bound (Rapoza, 1990).

Figure 19:
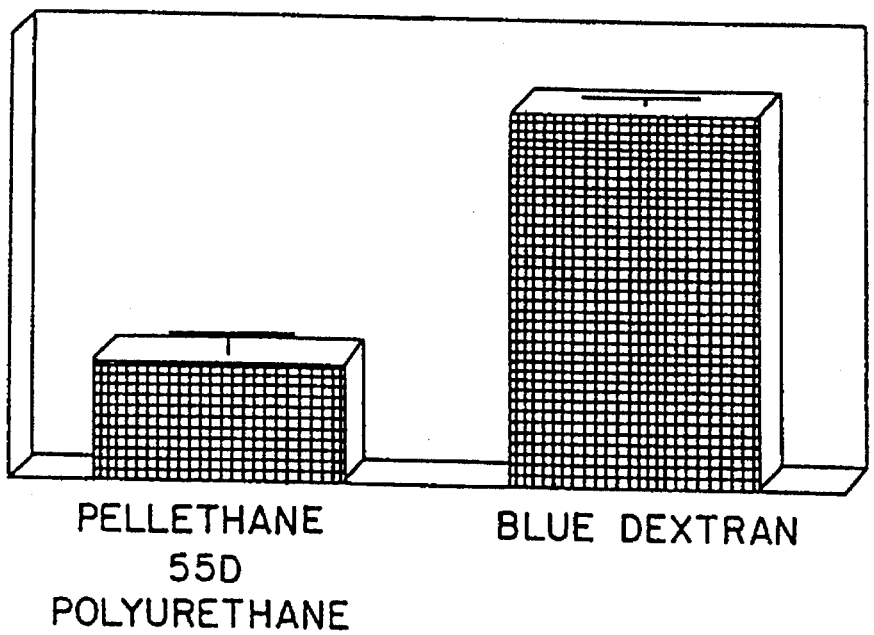
FIG. 19 is a graph showing the % of adsorbed albumin removed from Pellethane 55D polyurethane and Blue Dextran surface-coated Pelletbane 55D polyurethane samples during a 1% SDS wash.

Therefore, samples were incubated for five hours in $^{125}$I-albumin then removed and washed in a 1% SDS solution for one hour. As FIG. 19 shows, approximately 95% of the albumin initially adsorbed to Blue Dextran grafted surfaces was removed during the SDS wash. These results indicate adsorbed albumin does not denature and is reversibly bound on the Blue Dextran surface-coated samples. The binding site of albumin on Blue Dextran surface-coated samples was tested next.

EXAMPLE 20

The Binding Site of Albumin on Surface-Coated Material

Figure 20:
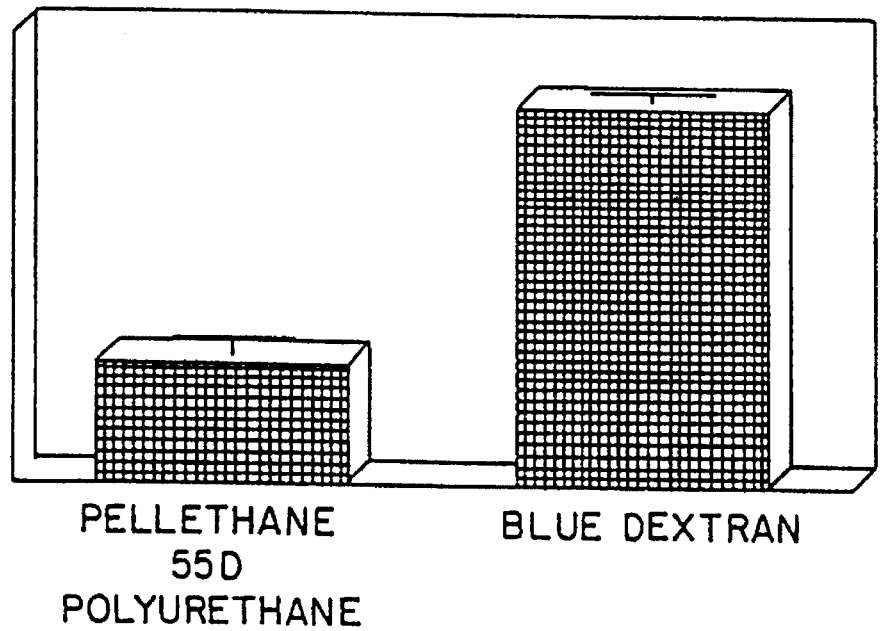
FIG. 20 is a graph showing the competitive displacement of $^{125}$I-albumin adsorbed on Blue Dextran surface-coated Pelletbane 55D polyurethane and uncoated Pellethane 55D polyurethane samples washed in either PBS or PBS containing Blue Dextran. Results are expressed as % of albumin removed from samples during Blue Dextran wash.

The binding site of albumin to Blue Dextran surface-coated Pellethane 55D was investigated by using sol-phase Blue Dextran to competitively block albumin binding to the Blue Dextran grafted to the surface of the polyurethane. Blue Dextran surface-coated and uncoated Pellethane 55D samples were rinsed in PBS for 15 minutes each prior to incubation in $^{125}$I-albumin (0.08 mg/ml) for 15 minutes. The samples were then washed in either PBS or PBS containing soluble Blue Dextran and counted in a scintillation counter. Results are given in FIG. 20. As can be seen in FIG. 20, the inclusion of Blue Dextran in the wash buffer selectively removed approximately 95% of the albumin adherent to surface-coated material. Therefore, albumin bound to surface-coated material is associated with the Blue Dextran on the surface.

EXAMPLE 21

Blood Loop Assay of Blue Dextran Surface-Coated Material

Pollethane 55D (2 mm in diameter and 30 cm in length) was surface-coated with Blue Dextran. A venipuncture was performed on a human subject without anticoagulant into a plastic syringe. One-milliliter aliquots of whole blood were then delivered immediately into a 12×75 mm glass test tube, an uncoated Pellethane 55D tubing sample. One end of each polyurethane tube was looped around and connected to the other end via a silicone connector. A stopwatch was started as soon as the blood entered the samples. The polyurethane tubes were then rotated at 9 rev/min until the blood clotted. The glass test tube was gently tilted every 30 seconds until a clot was seen; the stopwatch was stopped at these points and the time was recorded. The rate at which 1 ml of fresh whole blood clotted in the polyurethane tubes was compared to the rate of clotting in the glass tube. Results are shown in Table 11.

TABLE 11

Whole blood clotting times of a glass test tube, uncoated Pellethane 55D tubing and Blue Dextran surface-coated Pellethane 55D tubing.

| SAMPLE | CLOTTING TIME |
| --- | --- |
| Glass | 5 mins 32 secs |
| Uncoated Pellethane 55D | 9 mins 43 secs |
| Blue Dextran surface-coated Pellethane 55D | >16 hours |

The results in Table 11 indicate that both Blue Dextran surface-coated and uncoated tubing surfaces had an inhibitory effect on whole blood coagulation. However, the tubing that contained Blue Dextran had a large enough effect as to prevent complete clotting during the 16 hours it was allowed to rotate. Therefore, Blue Dextran surface-coating evidently decreases the thrombogenicity of Pelletbane 55D.

EXAMPLE 22

Following the clotting study, sodium dodecyl sulfate-polyacrylamide gel electrophoresis (SDS-PAGE) was performed on the polyurethane tubes to determine if there was an albumin coating on the surface of Blue Dextran surface-coated material. Both polyurethane surfaces were vigorously rinsed in PBS. The tubes were then cut into two pieces. One piece of each tube was placed in SDS-PAGE buffer solution and incubated overnight to remove the adherent protein. The buffer solution consisted of 62.5 mM Tris-HCl, 5% β-Mercaptoethanol, 10% glycerol and 2.3% SDS in DI water. SDS-PAGE was then performed on 100 μl of buffer solution containing the eluted proteins. following electrophoresis, the gel was stained with Coomassie Brilliant Blue, and the identity of the eluted proteins was determined by reference to molecular weight standards included on the gel. The results of this experiment indicate that the major protein adsorbed to Blue Dextran surface-coated material is albumin. By contrast, uncoated material had much less adsorbed albumin and proportionately more non-albumin proteins.

EXAMPLE 23

The other piece of each of the polyurethane tubings was placed in 2.5% glutaraldehyde solution overnight. Scanning electron microscopy was then used to examine the surface of each of the tubings. The SEM photographs demonstrated a lot of thrombus on the surface of the uncoated material. In contrast, there was no thrombus formation on the Blue Dextran coated surface. In fact, there was no apparent cellular adhesion of any kind. Therefore, the Blue Dextran surface coating technique decreased the thrombogenicity of the polyurethane surface. Next, the Blue Dextran surface coating was tested to see if it had any heparin-like activity.

EXAMPLE 24

ATIII Activity of Blue Dextran Surface-Coated Material

Clotting may be retarded on Blue Dextran surface-coated materials by the activation of ATIII by the three sulfonic acid groups per molecule of dye. This interaction may cause a heparin-like activation of ATIII.

Figure 21:
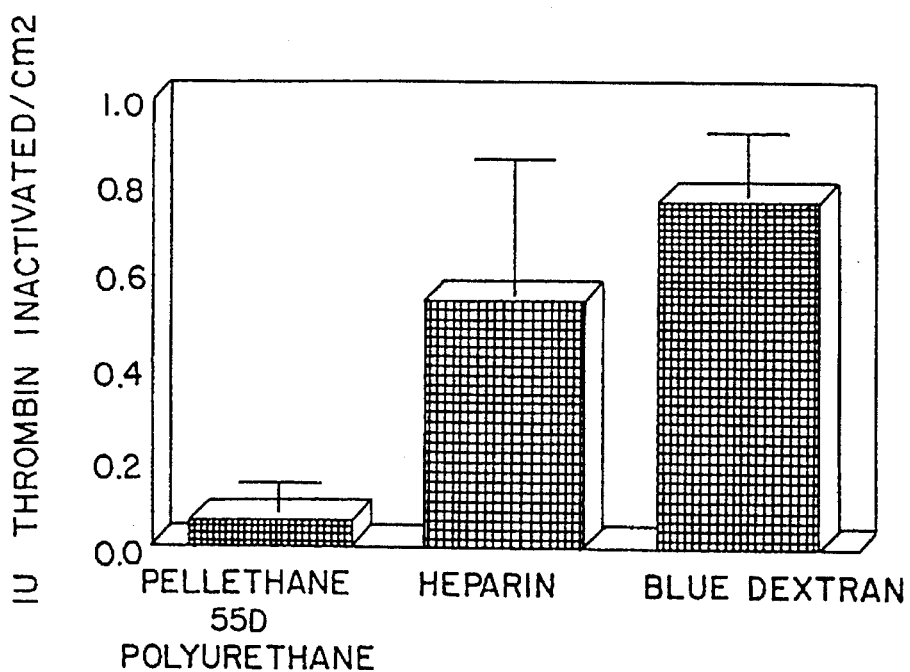
FIG. 21 is a graph showing a comparison of ATIII activity of uncoated Pellethane 55D polyurethane, CBAS (heparin) coated Pellethane 55D polyurethane and Blue Dextran surface-coated Pellethane 55D polyurethane samples. The results are expressed as the amount of thrombin inactivated by the sample surfaces/cm$^2$.

Therefore, the surface-mediated activation of ATIII by coated samples was assessed. Samples were first rinsed in PBS for 15 minutes prior to ATIII exposure. Following rinsing, the samples were exposed for 15 minutes to an excess of purified ATIII (50 IU/ml). Non-adsorbed ATIII is removed by rapid rinsing in tris-buffered saline, pH 7.4 at 25° C. (100 mM NaCl and 50 mM tris). The amount of surface bound and activated ATIII is then estimated by incubating the samples with an excess of thrombin. After a 10 minute incubation with constant mixing at 25° C., the residual thrombin was measured by reaction with a chromogenic substrate (H-D-phenylalanyl-L-pipecoly-L-arginine-p-nitroanilide dichloride) in a spectrophotometer. The change in absorbance at 405 nm was then measured. The results are given in FIG. 21. As the results demonstrate Blue Dextran surface coating appears to have some heparin-like effect. This heparin-like effect is presumably due to the Cibacron Blue dye in the Blue Dextran coating.

EXAMPLE 25

Bacterial Adherence to Blue Dextran Surface-Coated Material

The adherence of pathogenic bacteria to Blue Dextran surface coated and uncoated Pellethane 55D was investigated to determine the effectiveness of the Blue Dextran surface coating technique in preventing bacterial adherence. *Staphylococcus epidermidis* were chosen for the bacterial adhesion study since they are the most frequent cause of medical device associated infections.

*Staph. epidermidis* were grown overnight in Brain Heart Infusion. The bacteria were concentrated centrifugally and washed three times in isotonic saline solution. Bacteria were resuspended to $7 \times 10^6$ cfu/ml and samples of Blue Dextran surface-coated and uncoated Pellethane 55D were either immersed in the suspension with gentle mixing for two hours at 25° C. or pre-incubated in an albumin solution for 15 minutes followed by the two hour incubation in the bacterial solution. After incubation the samples were rinsed in sterile isotonic saline solution and then placed in 5 ml of sterile saline. The samples were then sonicated at 20 watts for one minute. After sonication 50 μl of solution, now containing displaced bacteria, were plated, incubated and counted. The results are given in FIG. 22.

The samples were stained and examined under a light microscope after sonication. There appeared to be no adherent bacteria left on the samples upon examination under the light microscope, indicating the sonication had knocked off the adherent bacteria.

Figure 22:
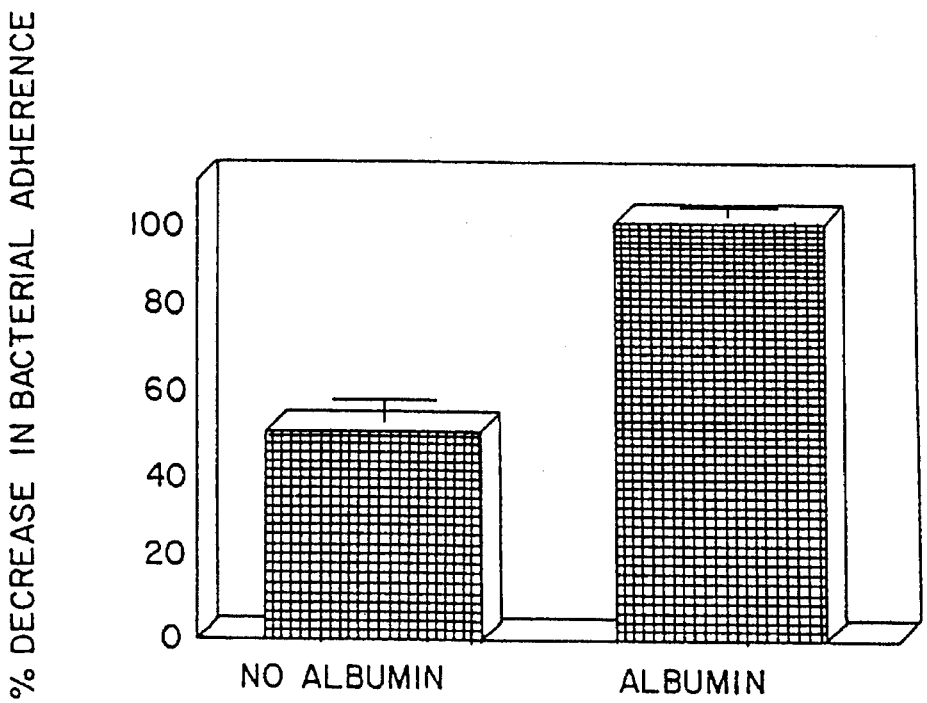
FIG. 22 is a graph showing percent decrease in bacterial adherence to Blue Dextran surface-derivatized Pallethane 55D compared to non-derivatized Pallethane 55D samples without albumin and with pre-albumin adsorption.

As the results in FIG. 22 indicate Blue Dextran surface coated material adhered approximately 50% fewer bacteria than did the uncoated material with no albumin present. This decrease is presumably due to the hydrophilic surface of the coated material. In the presence of albumin however, the Blue Dextran surface-coated material was able to decrease the bacterial adherence by almost 100%.

Summary of Blue Dextran Surface-Coating Technique

The Blue Dextran surface coating technique consists of the graft copolymerization of APMA/AAm to the polyurethane surface using CeIV ion. Dextran is then covalently attached to this hydrophilic coating through a Shiff base reaction. Cibacron Blue dye is then covalently attached to the bound dextran forming the Blue Dextran surface-coated polyurethane.

The binding of albumin to surface-coated material was shown to be approximately 95% specific and occurs even in the presence of fibrinogen. Second, it appears that the albumin which adsorbs to uncoated material has denatured and cannot be competitively displaced. In contract, 95% of the albumin bound to surface-coated material is readily displaced by a 1% SDS solution. Third, the binding of albumin to 95% of the surface-coated material's surface is evidently mediated primarily through site-specific binding of the protein to the Blue Dextran. This is supported by the observation that added (free) blue dextran will competitively release approximately 95% of the albumin pre-adsorbed to surface coated material.

The binding of albumin to Blue Dextran surface-coated material was shown to inhibit the surface activation of clotting, as measured by the whole blood clotting time, decrease the adherence of blood platelets and prevent the formation of fibrin on the surface. The Blue Dextran surface coating technique also was shown to adhere significantly fewer bacteria.

Thrombosis and infection are probably the two greatest hindrances to the utilization of artificial implantable medical devices. The materials of these devices tend to cause the formation of thrombi and serve as a focus for infection of the body by a number of bacterial species. Device-associated infections are promoted by the tendency of these organisms to adhere and colonize the surface of the device. Thrombus formation can be promoted by the adsorption of large amounts of cell adhesion proteins, i.e., fibrinogen, to the device surface. This adsorbed adhesive protein then interacts with the platelet membrane GPIIB-IIIa receptors and possibly GPIb receptors leading to platelet deposition and activation. The deposition and activation of platelets causes platelet aggregation and finally thrombus formation. To prevent thrombus formation and infection from occurring it was determined that an implantable material should posses an "active" surface which selectively and reversibly binds without denaturing albumin with high affinity. Therefore, a modification technique for increasing the albumin-binding ability of an implantable polyurethane was created.

The technique creates a biomaterial surface comprised of a high affinity albumin-binding dye to which albumin selectively and reversibly binds forming a renewable endogenous albumin coating on the surface when the material is in contact with a physiological fluid containing albumin. The formation of this albumin coating was demonstrated to diminish the tendency of the material to promote thrombosis on the material surface by preventing the cell adhesion proteins and the pro-coagulation proteins from adsorbing to the material surface. The coating also was demonstrated to diminish the tendency of the material to promote bacteria infection by decreasing the adherence and colonization of pathogenic bacteria to the material surface.

The modification technique provides a method of which approximately 95% of the material's surface selectively and reversibly binds albumin.

HEPARIN COATING

Figure 23:
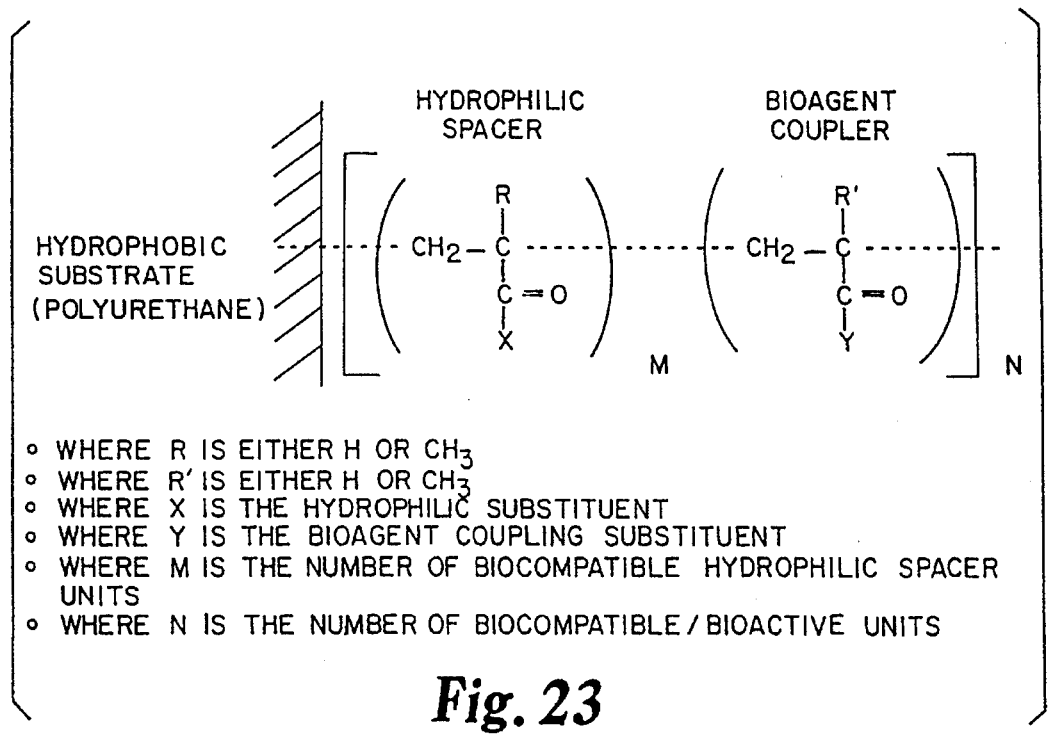
FIG. 23 is a schematic formula showing various monomers making up a polymer.

Grafting can be engineered stoichiometrically to produce surfaces containing the desired amount of hydrophilicity and the desired amount of bioagent couplers. Hydrophilic spacer monomers (neutral, anionic and cationic) can be selected to produce appropriately charged hydrophilic spacers. Bioagent coupling monomers can be selected based on pendant functional groups i.e., —OH, —NH$_2$, —CHO, —COOH, —NCO, needed or wanted from acrylic type monomers and is demonstrated in FIG. 23.

Graft copolymerization onto poly(ether urethane) with CeIV ion is the preferred medium. The monomers chosen to work with are acrylamide (AAm), acrylic acid (AA), 2-acrylamido- 2-methylpropane sulfonic acid (AMPS), 2-hydroxyethyl methacrylate (HEMA) and N-(3-aminopropyl) methacrylamide hydrochloride (APMA). These monomers were chosen based partly on their reactivity and water solubility characteristics. AAm, AA and AMPS monomers have been used as the biocompatible hydrophilic spacer monomerso HEMA and APMA monomers have been used as the bioagent coupling monomers. AAm has been used extensively as an affinity chromatographic matrix. AAm is a neutral hydrophilic monomer; therefore, polymers of AAm have shown little protein association. AMPS and AA are anionic hydrophilic monomers. Polymers of AMPS and copolymers of AMPS and AA have been shown to have a heparin-like activity. HEMA is a hydroxyl containing monomer and APMA is an amino containing monomer.

Grafting can be engineered stoichiometrically to produce surfaces containing the desired amount of hydrophilicity and the desired amount of couplers. Hydrophilic spacer monomers (neutral, anionic and cationic) can be selected to produce appropriately charged hydrophilic spacers. Coupling monomers can be selected based on pendant functional groups i.e., —OH, —NH$_2$, —CHO, —NCO needed or wanted for immobilizing heparin.

Either the AAm or AMPS monomer is used as the hydrophilic spacer monomer. The APMA monomer is used as the coupling monomer. AAm has been used extensively as an affinity chromatographic matrix. AAm is a neutral hydrophilic monomer, therefore, polymers of AAm have shown little protein association. APMA is an amino containing monomer, thus allowing the attachment of heparin.

Heparin is covalently attached to the amino groups on the APMA through a stabilized Schiff base reaction (reductive amination). The heparin is oxidized using either sodium periodate or nitrous acid. Both oxidation techniques form reactive aldehyde groups. These aldehyde groups react with the primary amines on APMA forming imines. The imines are stabilized using sodium cyanoborohydride.

The following Example 26 demonstrates a technique for heparinizing a polyurethane surface. Currently, the technique yields polyurethane surfaces having approximately 5 times the heparin activity of Carmeda® coated polyurethane surfaces. Chandler loops prepared with the heparinized surface described have demonstrated that the coating prevented blood coagulation during a 2 hour study.

EXAMPLE 26

Figure 9B:
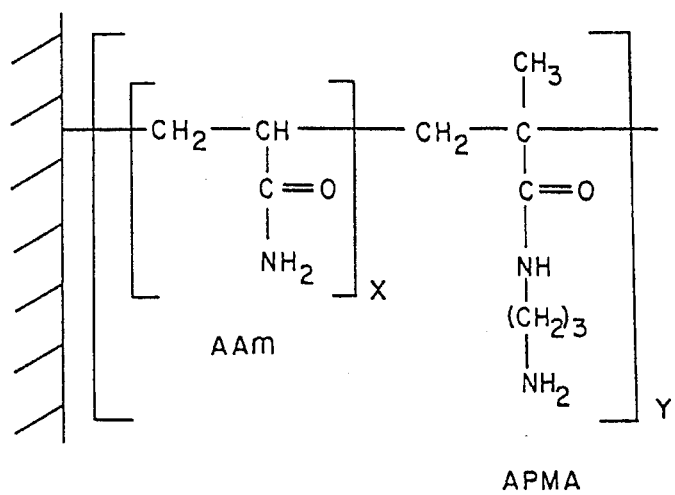
FIG. 9b shows the graft polymerization of AAm and APMA on a CeIV ion activated polyurethane surface.

The heparin surface coating technique begins with the graft copolymerization of acrylamide (AAm) and N-(3-aminopropyl)methacrylamide (APMA) monomers onto a clean polyurethane surface with CeIV ion. The CeIV ion creates a free radical on the polyurethane surface which initiates the graft copolymerization of the acrylamides (FIG. 9a and 9b). The amount of surface amination (the graft copolymerization of APMA and AAm) that takes place on the polyurethane surface can be measured via staining the surface with ponceau S dye, a negatively charged dye molecule. This dye ionically associates with primary amines on the aminated surfaced. After staining, the dye is released from the surface using SDS and quantified spectrophotometrically at 520 nm.

This aminated surface is then used for coupling heparin. The attachment of heparin consists of first oxidizing it with sodium m-periodate (NaIO4) thus forming aldehyde groups (FIG. 10). These aldehyde groups are then covalently attached to primary amino groups in the grafted APMA/AAm through reductive amination (Schiff base reaction) (FIG. 11). Sodium cyanoborohydride (NaCNBH$_3$) is used to stabilize the imine linkages (FIG. 12).

Figure 24:
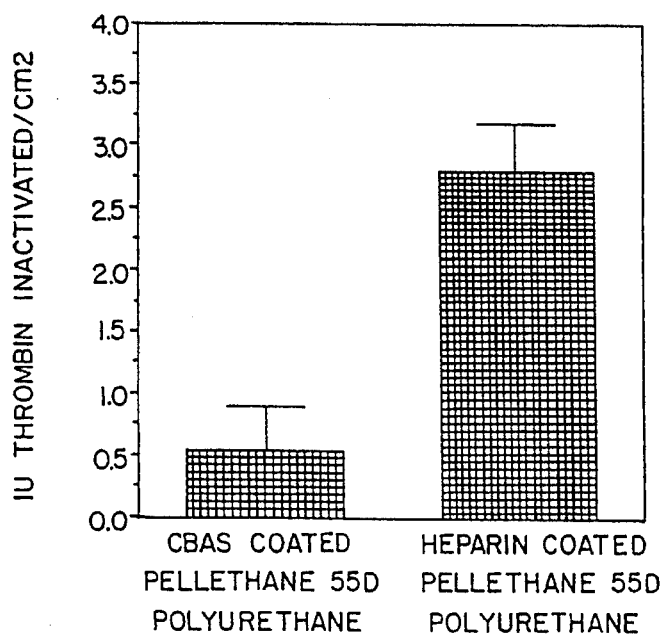
FIG. 24 is a graph showing the amount of IU Thrombin inactivated on the surface of CBAS coated Pellethane 55D polyurethane and heparin coated Pellethane 55D polyurethane.

The amount of heparin attached can be measured via staining the surface with toluidine blue dye, a positively charged dye that ionically associates with the negatively charged heparin. Toluidine blue is also released from the surface using SDS and is quantified spectrophotometrically at 640 nm. The heparin-activity of the surface is measured using a thrombin-ATIII activation assay. The assay begins by exposing heparin-derivatized samples to an excess of ATIII. Non-adsorbed ATIII is then removed by rapid rinsing in tris-buffered saline. The amount of surface bound and activated ATIII is then estimated by incubating the samples with an excess of thrombin. After incubation, the residual thrombin is measured by reaction with a chromogenic substrate in a spectrophotometer. The change in absorbance at 405 nm is measured. See FIG. 24 for the results.

EXAMPLE 27

The Cibacron Blue dye surface-derivatization technique begins with the graft polymerization of AMPS and HEMA monomers onto a polyurethane surface with CeIV ion. The CeIV ion creates a free radical on the polyurethane surface which initiates the graft copolymerization of the monomers. The HEMA monomer contains a hydroxyl group that is then used for coupling Cibacron Blue dye.

Polyurethane surfaces containing covalently coupled Cibacron Blue dye were prepared by first placing the polyurethane samples into the following degassed grafting solution for 2 hours at room temperature.

40 g 2-acrylamido-2-methylpropane sulfonic acid 10 g 2-hydroxyethyl methacrylate (HEMA)

1.1 g ceric ammonium nitrate 1.3 g nitric acid 70 ml DI water

Following grafting, the samples were rinsed thoroughly in DI water. The AMPS/HEMA grafted samples were then placed into a Cibacron Blue dye solution consisting of 1.0 g Cibacron Blue dye, 4.0 g NaCl, 12.0 g $NaHCO_3$ in 200 ml DI water overnight. The dyed samples were then thoroughly rinsed in DI water.

This completes the description of the preferred and alternate embodiments of the invention. Those skilled in the art may recognize other equivalents to the specific embodiments described herein which equivalents are intended to be encompassed by the claims attached hereto.

What is claimed is:

1. A method for administering a bioactive agent having a net ionic charge to a patient comprising the steps of:

(a) providing an implantable article having a polymeric surface;

(b) preparing an aqueous solution comprising as a first monomer, a water soluble monomer which includes pendant groups selected from the group consisting of amine groups and acid groups, said groups capable of imparting a net ionic charge in a graft polymer, and as a second monomer, a neutral, hydrophilic monomer;

(c) contacting the polymeric surface of the implantable article with the monomer solution for a period of time effective to provide a copolymer of the first and second monomers grafted to the surface, said copolymer having a net ionic charge;

(d) placing the bioactive agent having a net charge onto the grafted surface; and (e) implanting the article and bioactive agent into the patient's body in blood contact.

2. The method of claim 1 wherein the bioactive agent has the same net charge as the graft copolymer.

3. The method of claim 1 wherein the graft copolymer has a net (+) charge and the bioactive agent has a net (−) charge.

4. The method of claim 1 wherein the graft copolymer has a net (−) charge and the bioactive agent has a net (+) charge.

5. The method of claim 1 wherein the first monomer is selected from the group consisting of acrylic acid, 2-acrylamido-2-methylpropane sulfonic acid, and N-(3-aminopropyl) methacrylamide hydrochloride.

6. The method of claim 1 wherein the second monomer is acrylamide.

7. The method of claim 1 wherein the bioactive agent is a cationic antimicrobial compound.

8. The method of claim 7 wherein the cationic antimicrobial compound is selected from the group consisting of gentamycin, kanamycin, neomycin, silver ion, chlorhexidine, vancomycin, streptomycin and erythromycin.

\* \* \* \* \*